US008603145B2

(12) United States Patent
Forton et al.

(10) Patent No.: US 8,603,145 B2
(45) Date of Patent: Dec. 10, 2013

(54) COAXIALLY LOCKABLE POLY-AXIAL BONE FASTENER ASSEMBLIES

(75) Inventors: Charles R. Forton, Leander, TX (US);
Larry T. Khoo, Studio City, CA (US);
Peter Thomas Miller, Austin, TX (US);
Ryan Carter Harvey, Bordeaux (FR)

(73) Assignee: Zimmer Spine, Inc., Minneapolis, MN (US)

( * ) Notice: Subject to any disclaimer, the term of this patent is extended or adjusted under 35 U.S.C. 154(b) by 727 days.

(21) Appl. No.: 12/336,404

(22) Filed: Dec. 16, 2008

(65) Prior Publication Data

US 2010/0152785 A1    Jun. 17, 2010

(51) Int. Cl.
*A61B 17/70*    (2006.01)
*A61B 17/88*    (2006.01)
*A61F 2/28*     (2006.01)
*A61F 2/44*     (2006.01)

(52) U.S. Cl.
USPC ........... 606/272; 606/251; 606/266; 606/279; 606/264; 606/265; 623/16.11; 623/17.11

(58) Field of Classification Search
USPC .......... 623/17.11, 17.15, 17.16; 606/246–279
See application file for complete search history.

(56) References Cited

U.S. PATENT DOCUMENTS

| 6,368,321 | B1  |   | 4/2002  | Jackson              |         |
|-----------|-----|---|---------|----------------------|---------|
| 6,423,064 | B1  |   | 7/2002  | Kluger               |         |
| 6,530,929 | B1  |   | 3/2003  | Justis et al.        |         |
| 6,602,255 | B1  | * | 8/2003  | Campbell et al.      | 606/290 |
| 6,716,214 | B1  |   | 4/2004  | Jackson              |         |
| 6,979,334 | B2  | * | 12/2005 | Dalton               | 606/287 |
| 7,066,937 | B2  | * | 6/2006  | Shluzas              | 606/86 A|
| 7,144,396 | B2  | * | 12/2006 | Shluzas              | 606/266 |
| 7,250,052 | B2  |   | 7/2007  | Landry et al.        |         |
| 7,662,175 | B2  | * | 2/2010  | Jackson              | 606/300 |
| 7,682,377 | B2  | * | 3/2010  | Konieczynski et al.  | 606/269 |

(Continued)

FOREIGN PATENT DOCUMENTS

EP    1923011 A1    5/2008
FR    2763835       12/1998

OTHER PUBLICATIONS

European Extended Search Report for Application No. EP 09 015 565.6, completed Apr. 15, 2010, mailed, Aug. 17, 2010, 11 pages.

(Continued)

*Primary Examiner* — David Isabella
*Assistant Examiner* — Jacqueline Woznicki
(74) *Attorney, Agent, or Firm* — Seager, Tufte & Wickhem, LLC

(57) ABSTRACT

A poly-axial bone fastener assembly having a collar and a bone fastener can be coaxially locked to prevent poly-axial movements of the collar relative to the bone fastener while permitting the collar to rotate about an axis of the bone fastener, thereby combining the functions and advantages of a poly-axial bone screw and a fixed angle bone screw. Some embodiments of a coaxial locking mechanism may include a c-clip with a locking pin, a c-clip with hooks, a split ring with square corners, a pin that spins inside the collar, pins that travel about a neck of the bone fastener, a coaxially locking top that screws into the collar over a head of the bone fastener, and a top nut that threads onto the head of the bone fastener inside the collar to trap a flange of the collar between a shoulder of the bone fastener and the top nut.

14 Claims, 15 Drawing Sheets

(56) References Cited

U.S. PATENT DOCUMENTS

| | | |
|---|---|---|
| 2004/0225289 A1* | 11/2004 | Biedermann et al. ........... 606/61 |
| 2005/0228379 A1 | 10/2005 | Jackson |
| 2005/0228385 A1 | 10/2005 | Iott et al. |
| 2006/0084993 A1 | 4/2006 | Landry et al. |
| 2006/0142761 A1 | 6/2006 | Landry et al. |
| 2006/0200131 A1 | 9/2006 | Chao et al. |
| 2006/0241599 A1* | 10/2006 | Konieczynski et al. ........ 606/61 |
| 2006/0271046 A1 | 11/2006 | Kwak et al. |
| 2007/0123862 A1 | 5/2007 | Warnick |
| 2007/0219554 A1 | 9/2007 | Landry et al. |
| 2008/0009864 A1 | 1/2008 | Forton et al. |
| 2008/0039838 A1 | 2/2008 | Landry et al. |
| 2008/0077139 A1 | 3/2008 | Landry et al. |
| 2008/0086131 A1 | 4/2008 | Daly et al. |
| 2008/0097457 A1 | 4/2008 | Warnick |
| 2008/0108992 A1 | 5/2008 | Barry et al. |
| 2008/0114359 A1 | 5/2008 | Murner |
| 2008/0125816 A1 | 5/2008 | Jackson |
| 2008/0140135 A1 | 6/2008 | Konieczynski et al. |
| 2008/0172062 A1 | 7/2008 | Donahue et al. |
| 2008/0243185 A1* | 10/2008 | Felix et al. ..................... 606/246 |
| 2010/0063545 A1* | 3/2010 | Richelsoph .................. 606/264 |

OTHER PUBLICATIONS

European Search Report for Application No. EP 09015565, dated Apr. 26, 2010, completed Apr. 15, 2010, 6 pgs.

\* cited by examiner

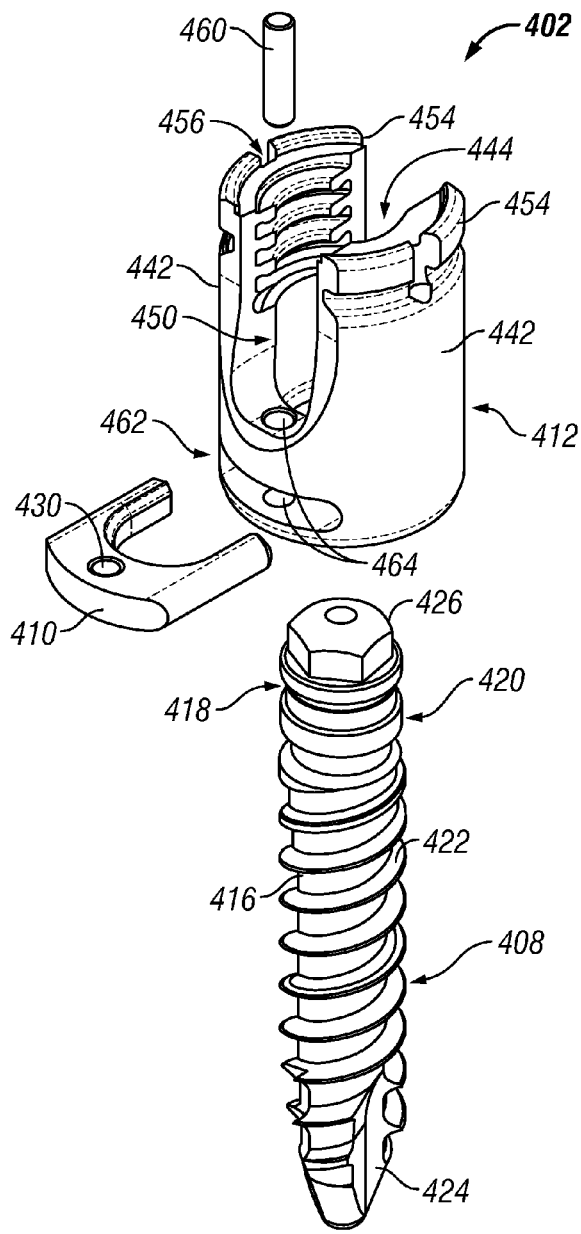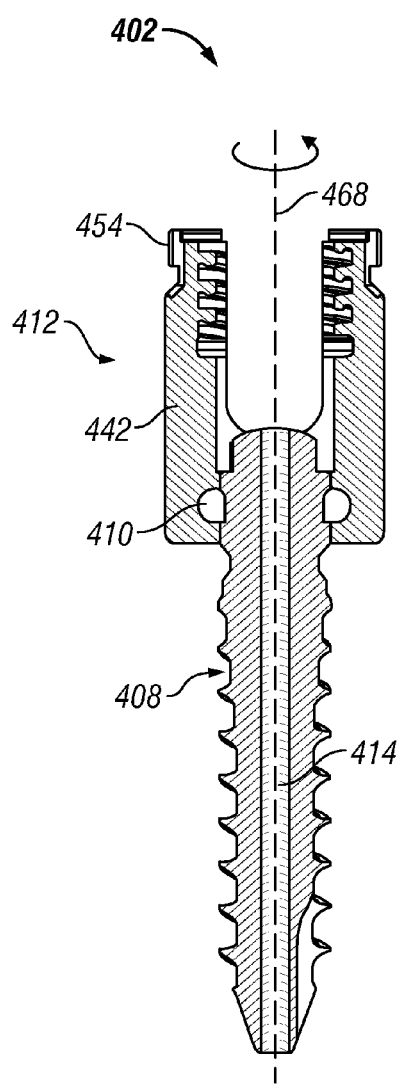
FIG. 14
FIG. 15

COAXIALLY LOCKABLE POLY-AXIAL BONE FASTENER ASSEMBLIES

CROSS-REFERENCE TO RELATED APPLICATION(S)

This application relates to U.S. patent application Ser. No. 11/284,282, entitled "SPINAL STABILIZATION SYSTEMS AND METHODS," filed on Nov. 21, 2005, which is pending, which is published as U.S. Patent Application Publication No. 20060084993, and which is a continuation of U.S. patent application Ser. No. 10/697,793, entitled "SPINAL STABILIZATION AND METHODS," filed Oct. 30, 2003, which claims priority to U.S. Provisional Application No. 60/422,455, entitled "SPINAL STABILIZATION SYSTEM USING POLY-AXIAL MEMBERS," filed Oct. 30, 2002; U.S. Provisional Application No. 60/466,091, entitled "SPINAL STABILIZATION SYSTEMS AND METHODS USING MINIMALLY INVASIVE SURGICAL PROCEDURES," filed Apr. 28, 2003; and U.S. Provisional Application No. 60/471,254, entitled "SPINAL STABILIZATION SYSTEMS AND METHODS USING MINIMALLY INVASIVE SURGICAL PROCEDURES," filed May 16, 2003. The above-referenced applications are incorporated by reference as if fully set forth herein.

BACKGROUND

1. Field of the Invention

The present invention generally relates to bone fasteners. More particularly, embodiments disclosed herein relate to coaxially lockable poly-axial bone fastener assemblies.

2. Description of Related Art

The human spine consists of segments known as vertebrae linked by intervertebral disks and held together by ligaments. There are 24 movable vertebrae—7 cervical (neck) vertebrae, 12 thoracic (chest) vertebrae, and 5 lumbar (back) veritebrae. Each vertebra has a somewhat cylindrical bony body (centrum), a number of winglike projections (procsses), and a bony arch. The arches are positioned so that the space they enclose forms the vertebral canal. The vertebral canal houses and protects the spinal cord, and within it the spinal fluid circulates. Ligaments and muscles are attached to various projections of the vertebrae. The bodies of the vertebrae form the supporting column of the skeleton. Fused vertebra make up the sacrum and coccyx, the very bottom of the vertebral column.

The spine is subject to abnormal curvature, injury, infections, tumor formation, arthritic disorders, and puncture or slippage of the cartilage disks. Degeneration caused by trauma, disease, and/or aging may destabilize a portion of the spine and affect surrounding structures. For example, a natural spacing between adjacent vertebrae may be altered due to the destabilization of the spine. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping.

Spinal stabilization systems for a lumbar region of the spine may be inserted during a spinal stabilization procedure using a posterior spinal approach. Conventional systems and methods for posterolateral spinal fusion may involve dissecting and retracting soft tissue proximate the surgical site. Dissection and retraction of soft tissue may cause trauma to the soft tissue, and extend recovery time. Minimally invasive procedures and systems may reduce recovery time as well as trauma to the soft tissue surrounding a stabilization site.

U.S. Pat. No. 6,530,929 to Justis et al. (hereinafter "Justis"), which is incorporated herein by reference, describes minimally invasive techniques and instruments for stabilizing a bony structure in an animal subject. Justis provides a method for using an instrument to connect at least two bone anchors with a connecting element. The instrument is secured to the anchors and manipulated to place the connecting element in a position more proximate the anchors.

In some spinal stabilization systems, pedicle screws can be used as bone anchors. In a traditional poly-axial pedicle screw, a spherical pocket or recess in the head of the screw is used to allow the shank of the screw to rotate in multiple directions about the spherical recess within the head of the screw.

U.S. Pat. No. 6,716,214 to Jackson (hereinafter "Jackson"), which is incorporated herein by reference, describes a poly-axial bone screw having a bone implantable shank, a head, and a retaining ring. The ring and the shank connect to form a ball and socket joint with the head and allow free rotation to a selected angular configuration. The ring has a restrictive neck and the angle of rotation of the ball and socket joint is only restricted by engagement of the shank neck with the ring restrictive neck on the head.

U.S. Patent Application Publication No. 2008/0097457 by Warnick (hereinafter "Warnick"), which is incorporated herein by reference, describes a pedicle screw system having a tulip assembly. Before a rod is placed in the tulip assembly, the tulip assembly may be locked onto a pedicle screw via a poly-axial lock. The poly-axial lock allows the tulip assembly to move poly-axially in relation to the screw.

U.S. Patent Application Publication No. 2008/0140135 by Konieczynski et al. (hereinafter "Konieczynski"), which is incorporated herein by reference, describes a poly-axial fixation device having a bone screw with a spherical head. A snap ring is utilized to frictionally engage the spherical head. The frictional forces created by the snap ring act on the spherical head to allow the bone screw to be set at a desired angular orientation with respect to a receiver member. The frictional forces can be overcome by grasping and moving the bone screw with respect to the receiver member to change the angular orientation.

SUMMARY OF THE DISCLOSURE

A spinal stabilization system may be installed in a patient to stabilize a portion of a spine. A spinal stabilization system may be installed using a minimally invasive procedure. A spinal stabilization system may be used to achieve rigid pedicle fixation while minimizing the amount of damage to surrounding tissue. In some embodiments, a spinal stabilization system may be used to provide stability to two or more vertebrae. A spinal stabilization system may include an elongated member, two or more bone fastener assemblies, and/or a closure member. The bone fastener assembly may include, but is not limited to, a bone fastener and a collar. A first portion of the bone fastener may couple to a portion of the spine. A first portion of a collar may couple to a second portion of the bone fastener. A second portion of the collar may couple to an elongated member. In some embodiments, an orientation of the bone fastener may be independent of the orientation of the collar for a bone fastener assembly. In some embodiments, a coaxial locking mechanism may lock the bone fastener and the collar to prevent poly-axial movements of the collar relative to the bone fastener while permitting the collar to rotate coaxially relative to the bone fastener. After the bone fastener is inserted or otherwise positioned in a vertebral body, a surgeon can apply corrective forces to the coaxially locked bone fastener assembly to move the vertebral body and rotate the collar coupled to the bone fastener about the axis of the bone fastener so that the elongated member can be positioned in the collar and in at least one other collar that is coupled to another vertebral body by a bone fastener.

In some embodiments, a coaxially lockable poly-axial bone fastener assembly comprises a bone fastener, a collar, and a coaxial locking mechanism for coaxially locking the bone fastener and the collar while allowing the collar to rotate about a central axis of the bone fastener. In some embodiments, the bone fastener is a poly-axial pedicle screw. More specifically, in some embodiments, prior to or during a minimally invasive procedure, a poly-axial bone fastener assembly having a collar and a bone fastener can be converted into a mono-axial bone fastener assembly via a coaxial locking mechanism. The coaxial locking mechanism locks the collar and the bone fastener in a manner to prevent poly-axial movements of the collar relative to the bone fastener while permitting the collar to rotate about an axis of the bone fastener. As will be described below in more details, some embodiments of a coaxial locking mechanism may include a c-clip with a locking pin, a c-clip with hooks, a split ring with square corners, a pin that spins inside the collar, pins that travel about a neck of the bone fastener, a coaxially locking top that screws into the collar over a head of the bone fastener, and a top nut that threads onto the head of the bone fastener inside the collar to trap a flange of the collar between a shoulder of the bone fastener and the top nut.

Because the collar and the bone fastener are locked coaxially, the collar can be rotated independent of the bone fastener without affecting the depth of the bone fastener in the vertebral body. A coaxially locked bone fastener assembly, with a bone fastener thereof inserted in a vertebral body, can function as a mono-axial bone fastener with an axial alignment and allow a surgeon to apply corrective forces to move the vertebral body in an efficient, effective, and minimally invasive manner. Embodiments of a coaxially lockable poly-axial bone fastener assembly disclosed herein can therefore combine the functions and advantages of a poly-axial bone fastener and a mono-axial bone fastener.

Other objects and advantages of the embodiments disclosed herein will be better appreciated and understood when considered in conjunction with the following description and the accompanying drawings.

BRIEF DESCRIPTION OF THE DRAWINGS

A more complete understanding of the present invention and the advantages thereof may be acquired by referring to the following description, taken in conjunction with the accompanying drawings in which like reference numbers indicate like features.

FIG. 14 depicts a perspective view of an embodiment of a bone fastener assembly and an embodiment of a coaxial locking mechanism.

FIG. 15 depicts a cross-sectional view of an embodiment of a bone fastener assembly with a coaxial locking mechanism.

Figure 1:
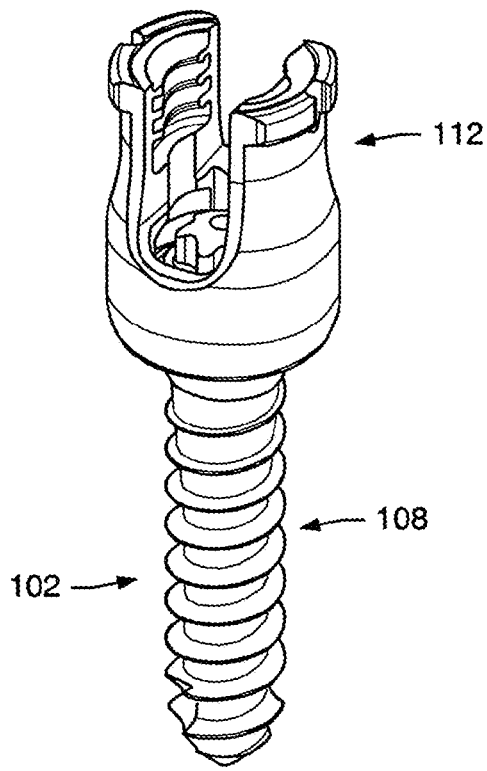
FIG. 1 depicts a perspective view of an embodiment of a bone fastener assembly.

While this disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but to the contrary, the intention is to cover all modifications, equivalents and alternatives falling within the spirit and scope of the present disclosure as defined by the appended claims.

DETAILED DESCRIPTION

Embodiments of a coaxially lockable poly-axial bone fastener assembly and the various features and advantageous details thereof are explained more fully with reference to the non-limiting embodiments detailed in the following description. Descriptions of well known starting materials, manufacturing techniques, components and equipment are omitted so as not to unnecessarily obscure the invention in detail. Skilled artisans should understand, however, that the detailed description and the specific examples shown in the drawings, while disclosing preferred embodiments of the invention, are given by way of illustration only and not by way of limitation. Various substitutions, modifications, and additions within the scope of the underlying inventive concept(s) will become apparent to those skilled in the art after reading this disclosure. Skilled artisans can also appreciate that the drawings disclosed herein are not necessarily drawn to scale.

As used herein, the terms "comprises," "comprising," includes, "including," "has," "having" or any other variation thereof, are intended to cover a non-exclusive inclusion. For example, a process, product, article, or apparatus that comprises a list of elements is not necessarily limited to only those elements, but may include other elements not expressly listed or inherent to such process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to a particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like.

A spinal stabilization system may be installed in a patient to stabilize a portion of a spine. Spinal stabilization may be used, but is not limited to use, in patients having degenerative disc disease, spinal stenosis, spondylolisthesis, pseudoarthrosis, and/or spinal deformities; in patients having fracture or other vertebral trauma; and in patients after tumor resection. A spinal stabilization system may be installed using a minimally invasive procedure. An instrumentation set may include instruments and spinal stabilization system components for forming a spinal stabilization system in a patient.

A minimally invasive procedure may be used to limit an amount of trauma to soft tissue surrounding vertebrae that are to be stabilized. In some embodiments, the natural flexibility of skin and soft tissue may be used to limit the length and/or depth of an incision or incisions needed during the stabilization procedure. Minimally invasive procedures may provide limited direct visibility in vivo. Forming a spinal stabilization system using a minimally invasive procedure may include using tools to position system components in the body.

A minimally invasive procedure may be performed after installation of one or more spinal implants in a patient. The spinal implant or spinal implants may be inserted using an anterior procedure and/or a lateral procedure. The patient may be turned and a minimally invasive procedure may be used to install a posterior spinal stabilization system. A minimally invasive procedure for stabilizing the spine may be performed without prior insertion of one or more spinal implants in some patients. In some patients, a minimally invasive procedure may be used to install a spinal stabilization system after one or more spinal implants are inserted using a posterior spinal approach.

Various instruments may be used in a minimally invasive procedure to form a spinal stabilization system in a patient. The instruments may include, but are not limited to, positioning needles, guide wires, dilators, bone awls, bone taps, sleeves, drivers, tissue wedges, elongated member length estimating tools, mallets, tissue retractors, and tissue dilators. The instruments may be provided in an instrumentation set. The instrumentation set may also include components of the spinal stabilization system. The components of the spinal stabilization system may include, but are not limited to, bone fastener assemblies of various sizes and/or lengths, elongated members, and closure members.

Instruments used to install a spinal stabilization system may be made of materials including, but not limited to, stainless steel, titanium, titanium alloys, ceramics, and/or polymers. Some instruments may be autoclaved and/or chemically sterilized. Some instruments may include components that cannot be autoclaved or chemically sterilized. Components of instruments that cannot be autoclaved or chemically sterilized may be made of sterile materials. The sterile materials may be placed in working relation to other parts of the instrument that have been sterilized.

Components of spinal stabilization systems may be made of materials including, but not limited to, titanium, titanium alloys, stainless steel, ceramics, and/or polymers. Some components of a spinal stabilization system may be autoclaved and/or chemically sterilized. Components that may not be autoclaved and/or chemically sterilized may be made of sterile materials. Components made of sterile materials may be placed in working relation to other sterile components during assembly of a spinal stabilization system.

A spinal stabilization system may be used to achieve rigid pedicle fixation while minimizing the amount of damage to surrounding tissue. In some embodiments, a spinal stabilization system may be used to provide stability to two adjacent vertebrae (i.e., one vertebral level). A spinal stabilization system may include two bone fastener assemblies. One bone fastener assembly may be positioned in each of the vertebrae to be stabilized. An elongated member may be coupled and secured to the bone fastener assemblies. As used herein, "coupled" components may directly contact each other or may be separated by one or more intervening members.

In some embodiments, a spinal stabilization system may provide stability to three or more vertebrae (i.e., two or more vertebral levels). In a two vertebral level spinal stabilization system, the spinal stabilization system may include three bone fastener assemblies. One bone fastener assembly may be positioned in each of the vertebrae to be stabilized. An elongated member may be coupled and secured to the three bone fastener assemblies. In some embodiments, a single two-level spinal stabilization system may be installed in a patient. Such a system may be referred to as a unilateral, two-level stabilization system or a two-level, three-point stabilization system. In some embodiments, two three-point spinal stabilization systems may be installed in a patient on opposite sides of a spine. Such a system may be referred to as a bilateral, two-level stabilization system or a two-level, six-point stabilization system.

In some embodiments, combination systems may be installed. For example, a two-point stabilization system may be installed on one side of a spine, and a three-point stabilization system may be installed on the opposite side of the spine. The composite system may be referred to a five-point stabilizatoin system.

Minimally invasive procedures may reduce trauma to soft tissue surrounding vertebrae that are to be stabilized as only a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized. In some embodiments, the incision may be above and between the vertebrae to be stabilized. In some embodiments, the incision may be above and substantially halfway between the vertebrae to be stabilized. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures. A minimally invasive procedure may reduce recovery time for the patient as compared to invasive spinal procedures.

Spinal stabilization systems may be used to correct problems in lumbar, thoracic, and/or cervical portions of a spine. Various embodiments of a spinal stabilization system may be used from the C1 vertebra to the sacrum. For example, a spinal stabilization system may be implanted posterior to the spine to maintain distraction between adjacent vertebral bodies in a lumbar portion of the spine. Such a spinal stabilization system may include bone fastener assemblies, one or more elongated members to connect the bone fastener assemblies, and closure members to secure the elongated members onto the bone fastener assemblies. Other spinal stabilization system embodiments may include, but are not limited to, plates, dumbbell-shaped members, and/or transverse connectors. Readers are directed to the above-referenced U.S. Pat. No. 7,250,052, for additional teachings on spinal stabilization systems.

A bone fastener may be, but is not limited to, a bone screw, a ring shank fastener, a barb, a nail, a brad, or a trocar. Bone fasteners and/or bone fastener assemblies may be provided in various lengths in an instrumentation set to accommodate variability in vertebral bodies. For example, an instrumentation set for stabilizing vertebrae in a lumbar region of the spine may include bone fastener assemblies with lengths ranging from about 30 mm to about 75 mm in 5 mm increments. A bone fastener assembly may be stamped with indicia (i.e., printing on a side of the collar). In some embodiments, a bone fastener assembly or a bone fastener may be color-coded to indicate a length of the bone fastener. In certain embodiments, a bone fastener with a 30 mm thread length may have a magenta color, a bone fastener with a 35 mm thread length may have an orange color, and a bone fastener with a 55 mm thread length may have a blue color. Other colors may be used as desired.

Each bone fastener provided in an instrumentation set may have substantially the same thread profile and thread pitch. In an embodiment, the thread may have about a 4 mm major diameter and about a 2.5 mm minor diameter with a cancellous thread profile. In certain embodiments, the minor diameter of the thread may be in a range from about 1.5 mm to about 4 mm or larger. In certain embodiments, the major diameter of the thread may be in a range from about 3.5 mm to about 6.5 mm or larger. Bone fasteners with other thread dimensions and/or thread profiles may also be used. A thread profile of the bone fasteners may allow bone purchase to be maximized when the bone fastener is positioned in vertebral bone.

Figure 2:
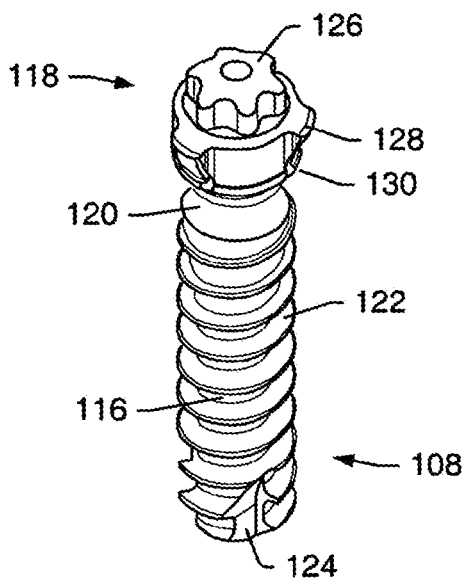
FIG. 2 depicts a perspective view of an embodiment of a bone fastener.
Figure 3:
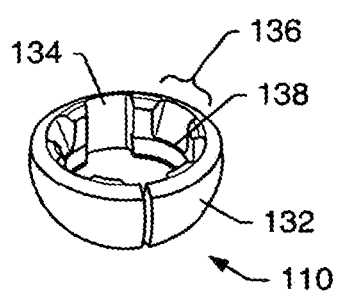
FIG. 3 depicts a perspective view of an embodiment of a bone fastener assembly ring.
Figure 4:
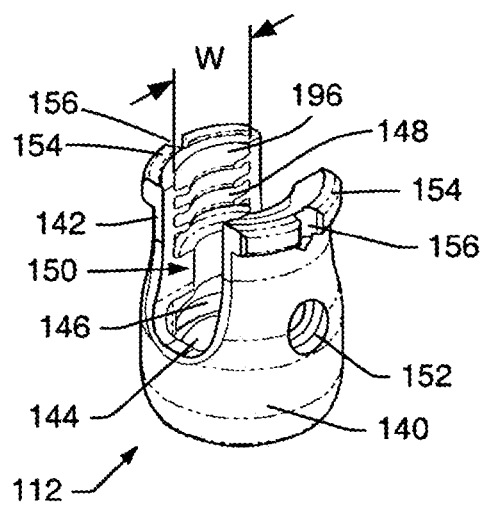
FIG. 4 depicts a perspective view of an embodiment of a bone fastener assembly collar.

FIG. 1 depicts a perspective view of an embodiment of bone fastener assembly 102 that may be implanted to stabilize a portion of a spine using a minimally invasive surgical procedure. FIGS. 2-4 depict embodiments of bone fastener assembly components. Components of bone fastener assembly 102 may include, but are not limited to, bone fastener 108 (shown in FIG. 2), ring 110 (shown in FIG. 3), and collar 112 (shown in FIG. 4).

FIG. 2 depicts a perspective view of an embodiment of bone fastener 108. Bone fastener 108 may couple bone fastener assembly 102 to a vertebra. Bone fastener 108 may include shank 116, head 118, and neck 120. Shank 116 may include threading 122. In some embodiments, threading 122 may include self-tapping start 124. Self-tapping start 124 may facilitate insertion of bone fastener 108 into vertebral bone.

Head 118 of bone fastener 108 may include various configurations to engage a driver that inserts the bone fastener into a vertebra. In some embodiments, the driver may also be used to remove an installed bone fastener from a vertebra. In some embodiments, head 118 may include one or more tool portions 126. Tool portions 126 may be recesses and/or protrusions designed to engage a portion of the driver. In some embodiments, bone fastener 108 may be cannulated for use in a minimally invasive procedure.

Head 118 of bone fastener 108 may include one or more splines 128, as depicted in FIG. 2. In some head embodiments, head 118 may include three splines. Splines 128 may be equally spaced circumferentially around head 118 of bone fastener 108. In some head embodiments, splines 128 may be spaced at unequal distances circumferentially around head 118. Splines 128 may include various surface configurations and/or texturing to enhance coupling of bone fastener 108 with a ring of a bone fastener assembly. In some embodiments, sides of the splines may be tapered so that the splines form a dovetail connection with a ring. In some embodiments, spline width may be tapered so that a good interference connection is established when the bone screw is coupled to a ring. Splines 128 may include one or more projections 130 to facilitate coupling bone fastener 108 with an inner surface of a ring. In some embodiments, projections 130 may be positioned on a lower portion of splines 128. In some embodiments, the splines may include recessed surfaces that accept projections extending from surfaces of the ring.

Neck 120 of bone fastener 108 may have a smaller diameter than adjacent portions of head 118 and shank 116. The diameter of neck 120 may fix the maximum angle that the collar of the bone fastener assembly can be rotated relative to bone fastener 108. In some embodiments, neck 120 may be sized to allow up to about 40 degrees or more of angulation of the collar relative to the bone fastener. In some embodiments, the neck may be sized to allow up to about 30 degrees of angulation of the collar relative to the bone fastener. In some embodiments, the neck may be sized to allow up to about 20 degrees of angulation of the collar relative to the bone fastener.

FIG. 3 depicts a perspective view of an embodiment of a bone fastener assembly ring. Ring 110 may be positioned between head 118 of bone fastener 108 and collar 112. Outer surface 132 of ring 110 may have a contour that substantially complements a contour of an inner surface of a collar in which the ring resides. A contour of the outer surface of the ring may be a spherical portion. When the ring is positioned in the collar, the complementary shape of the ring outer surface and the inner surface of the collar that contacts the ring allows angulation of the collar relative to a bone fastener coupled to the ring. The contour of the outer surface of the ring and the inner surface of the collar may inhibit removal of the ring from the collar after insertion of the ring into the collar.

Outer surface 132 of ring 110 may have a smooth finish. In some embodiments, outer surface 132 may be surface treated or include coatings and/or coverings. Surface treatments, coatings, and/or coverings may be used to adjust frictional and/or wear properties of the outer surface of the ring. In some embodiments, a portion of the outer surface of the ring may be shaped and/or textured to limit a range of motion of the collar relative to a bone fastener of a bone fastener assembly.

An inner surface of ring 110 may include one or more grooves 134 and/or one or more seats 136. Seats 136 may be circumferentially offset from grooves 134. Grooves 134 may be sized to allow passage of splines of a bone fastener (e.g., splines 128 shown in FIG. 2) through the ring. When the splines are inserted through grooves 134, the bone fastener may be rotated until the splines align with seats 136. The bone fastener may be pulled or driven so that the splines are positioned in seats 136. In some embodiments, projections (e.g., projections 130 in FIG. 2) may pass over ridges 138 of ring 110. Passage of the projections over ridges 138 may securely couple the bone fastener to the ring and inhibit separation of the ring from the bone fastener.

In a ring embodiment, a number of grooves 134 and a number of seats 136 may equal a number of splines 128 on head 118 of bone fastener 108. Seats 136 and grooves 134 may be equally spaced circumferentially around the inner surface of ring 110. In some embodiments, seats 136 may be circumferentially offset about 60 degrees from grooves 134.

In some embodiments, a bone fastener assembly ring may be a complete ring without a split or slots. In some embodiments, a ring may include a split or slots to facilitate insertion of the ring into a collar. FIG. 3 depicts an example of ring 110 with a split. In some embodiments, a ring with a split and/or slots may be compressed to ease insertion into a collar. Once positioned in the collar, the ring may expand to its original uncompressed dimensions, thus inhibiting removal from the collar.

As used herein, the term "collar" includes any element that wholly or partially encloses or receives one or more other elements. A collar may enclose or receive elements including, but not limited to, a bone fastener, a closure member, a ring, and/or an elongated member. In some embodiments, a collar may couple two or more other elements together (e.g., an elongated member and a bone fastener). A collar may have any of various physical forms. In some embodiments, a collar may have a "U" shape. However, it is to be understood that a collar may also have other shapes.

A collar may be open or closed. A collar having a slot and an open top may be referred to as an "open collar" or a "tulip head." A bone fastener assembly that includes an open collar may be referred to as an "open fastener." In some embodiments, an elongated member may be top loaded into the open fastener. A closure member may be coupled to the collar to secure the elongated member to the open fastener.

A collar that does not include a slot and an open top may be referred to as a "closed collar." A spinal implant that includes a closed collar may be referred to as a "closed implant." A closed collar may include an aperture, bore, or other feature in side surfaces for accommodating other components of a stabilization system (e.g., an elongated member). A setscrew may be used to securely couple an elongated member to a closed implant.

FIG. 4 depicts a perspective view of an embodiment of a bone fastener assembly collar. Collar 112 may include body 140 and arms 142. Arms 142 may extend from body 140. Body 140 of collar 112 may be greater in width than a width across arms 142 of collar 112 (i.e., body 140 may have a maximum effective outer diameter greater than a maximum effective outer diameter of arms 142). A reduced width across arms 142 may allow a detachable member to be coupled to the arms without substantially increasing a maximum effective outer diameter along a length of collar 112. Thus, a reduced width across arms 142 may reduce bulk at a surgical site.

A height of body 140 may range from about 3 millimeters (mm) to about 7 mm. In an embodiment, a height of body 140 is about 5 mm. Body 140 may include opening 144 in a lower surface of the body. To inhibit passage of a ring from collar 112, opening 144 may be smaller than an outer diameter of the ring. Inner surface 146 may be machined to complement a portion of an outer surface of a ring that is to be positioned in collar 112. Machining of inner surface 146 may enhance retention of a ring in collar 112. Inner surface 146 of body 140 may be complementary in shape to a portion of outer surface 132 of ring 110 (see FIG. 4) so that the ring is able to swivel in the collar. Inner surfaces and/or outer surfaces of collar 112 may be surface treated or include coatings and/or coverings to modify frictional properties or other properties of the collar.

Inner surfaces of arms 142 may include modified thread 148. Modified threads 148 may engage complementary modified threads of a closure member to secure an elongated member to a bone fastener assembly. Modified threads 148 may have a constant pitch or a variable pitch.

A height and a width of arms 142 may vary. Arms 142 may range in height from about 8 mm to about 15 mm. In an embodiment, a height of arms 142 is about 11 mm. A width (i.e., effective diameter) of arms 142 may range from about 5 mm to 14 mm. Arms 142 and body 140 may form slot 150. Slot 150 may be sized to receive an elongated member. Slot 150 may include, but is not limited to, an elongated opening of constant width, an elongated opening of variable width, a rectangular opening, a trapezoidal opening, a circular opening, a square opening, an ovoid opening, an egg-shaped opening, a tapered opening, and combinations and/or portions thereof. In some embodiments, a first portion of slot 150 may have different dimensions than a second portion of slot 150. In certain embodiments, a portion of slot 150 in first arm 142 may have different dimensions than a portion of slot 150 in second arm 142. When an elongated member is positioned in slot 150, a portion of the elongated member may contact a head of a bone fastener positioned in the collar.

In an embodiment of a collar, arms 142 of collar 112 may include one or more openings and/or indentions 152. Indentions 152 may vary in size and shape (e.g., circular, triangular, rectangular). Indentions 152 may be position markers and/or force application regions for instruments that perform reduction, compression, or distraction of adjacent vertebrae. In some embodiments, openings and/or indentions may be positioned in the body of the collar.

Arms 142 may include ridges or flanges 154. Flange 154 may allow collar 112 to be coupled to a detachable member so that translational motion of the collar relative to the detachable member is inhibited. Flanges 154 may also include notches 156. A movable member of a detachable sleeve may extend into notch 156. When the movable member is positioned in notch 156, a channel in the sleeve may align with a slot in collar 112. With the movable member positioned in notch 156, rotational movement of collar 112 relative to the detachable member may be inhibited.

Figure 5:
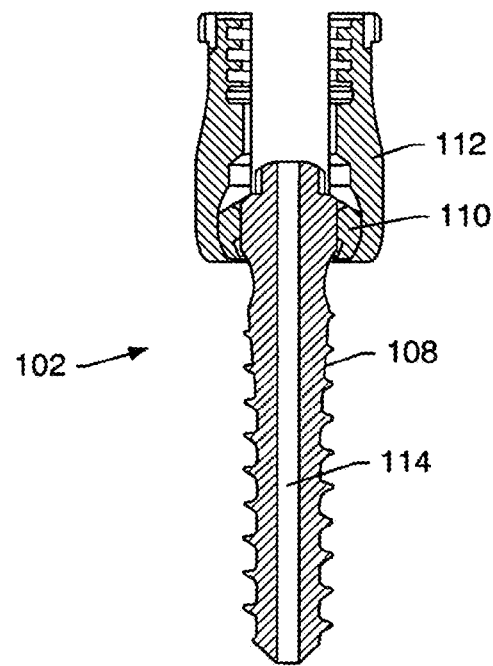
FIG. 5 depicts a cross-sectional view of an embodiment of a bone fastener assembly.

FIG. 5 depicts a cross-sectional view of an embodiment of bone fastener assembly 102 comprising bone fastener 108, ring 110, and collar 112. Bone fastener 108 of bone fastener assembly 102 may include passage 114. Bone fastener 108 may be cannulated (i.e., passage 114 may run through the full length of the bone fastener). A guide wire may be placed through passage 114 so that bone fastener 108 may be inserted into a vertebra at a desired location and in a desired angular orientation relative to the vertebra with limited or no visibility of the vertebra.

Figure 6:
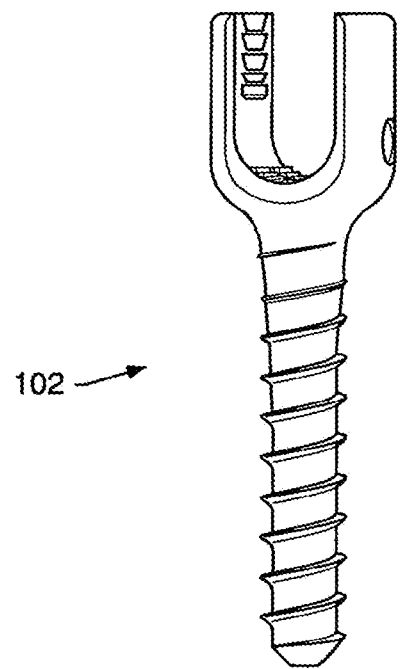
FIG. 6 depicts a perspective view of an embodiment of a bone fastener assembly.

In some embodiments, a bone fastener assembly may be a fixed angle fastener. FIG. 6 depicts a perspective view of an embodiment of a fixed angle bone fastener 102. Fixed angle bone fastener 102 may be formed as a unitary piece of metal. In this case, the head portion and the shank portion of bone fastener 102 are fixed. A fixed angle fastener may be positioned as the first bone fastener assembly inserted into a vertebra.

Figure 7A:
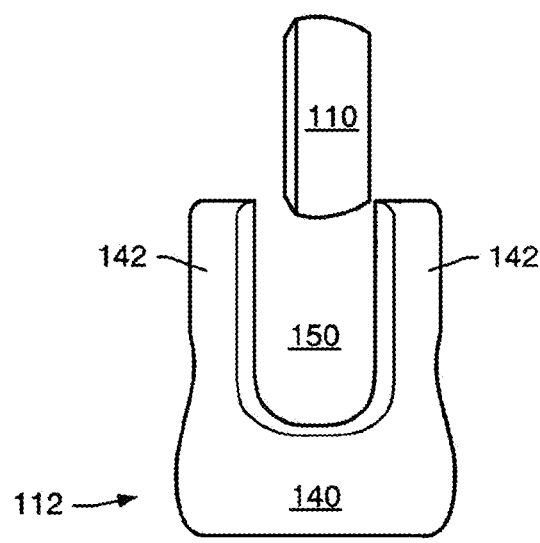
FIGS. 7A-7C depict schematic views of a method of positioning a ring in a collar of a bone fastener assembly.
Figure 7B:
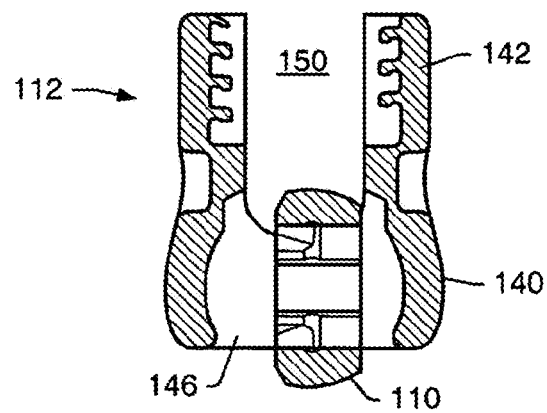
Figure 7C:
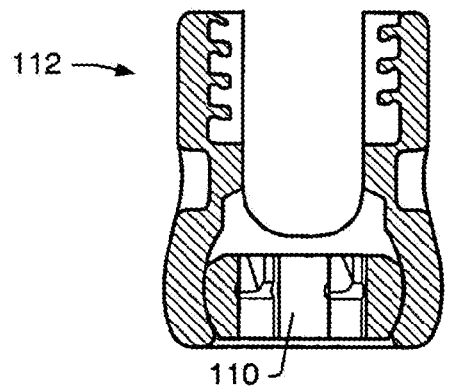

FIGS. 7A-7C show views of collar 112 and ring 110 during top loading insertion of the ring into the collar. Ring 110 may be positioned as shown in FIG. 7A and inserted past arms 142 into body 140. FIG. 7B depicts a cross-sectional view of ring 110 and collar 112 after insertion of the ring into the collar through slot 150. After insertion of ring 110 into collar 112, the ring may be rotated within the collar so that a bone fastener may be positioned through the ring. FIG. 7C depicts a cross-sectional view of ring 110 and collar 112 after rotation of the ring in the collar.

Figure 8A:
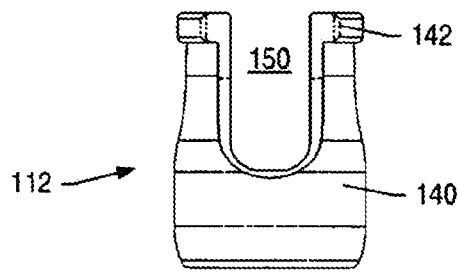
FIGS. 8A-8C depict schematic views of a method of positioning a ring in a collar of a bone fastener assembly.
Figure 8A:
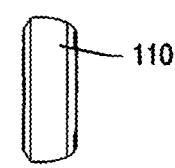
Figure 8B:
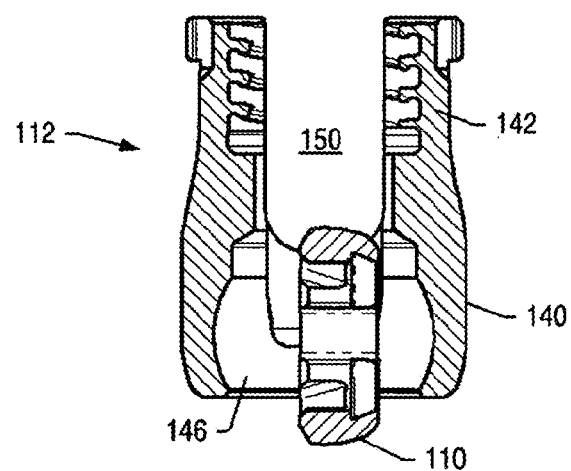
Figure 8C:
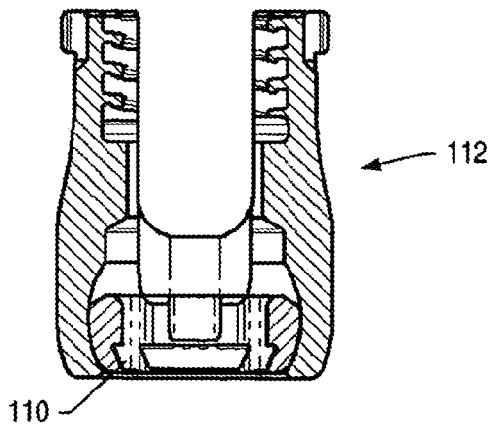

FIGS. 8A-8C show views of collar 112 and ring 110 during bottom loading insertion of the ring into the collar. Ring 110 may be positioned as shown in FIG. 8A and inserted into body 140 through an opening in the bottom of collar 112. In some embodiments, ring 110 may be inserted into body 140 through a groove or a slot in the bottom of collar 112. In certain embodiments, collar 112 designed for bottom insertion of ring 110 may have narrower slot 150 than a collar designed for top insertion of a ring. Collar 112 with narrower slot 150 may allow an elongated member with a reduced diameter to be used in a spinal stabilization system. Collar 112 with narrower slot 150 may be used to reduce bulk at a surgical site. FIG. 8B depicts a cross-sectional view of ring 110 and collar 112 after insertion of the ring into the collar through the opening in the bottom of the collar. After insertion of ring 110 into collar 112, the ring may be rotated so that a bone fastener may be positioned through the ring. Tolerance between an outer surface of ring 110 and an inner surface of body 140 shown in FIGS. 7A-7C and 8A-8C may require force to be applied to the ring to drive the ring into the body. Once ring 110 is positioned in body 140, the ring may expand slightly. In certain embodiments, significant force may be required to remove ring 110 from body 140 (i.e., the ring may be substantially unreleasable from the body). The required force may inhibit unintentional removal of ring 110 from body 140. FIG. 8C depicts a cross-sectional view of ring 110 and collar 112 after rotation of the ring in the collar.

Figure 9A:
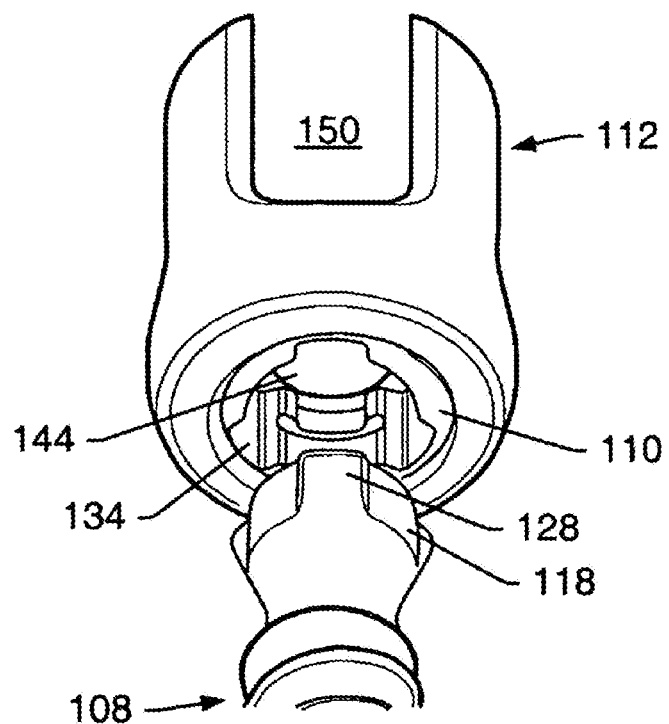
FIGS. 9A-9B depict schematic views of positioning a bone fastener in a ring and a collar to form a bone fastener assembly.
Figure 9B:
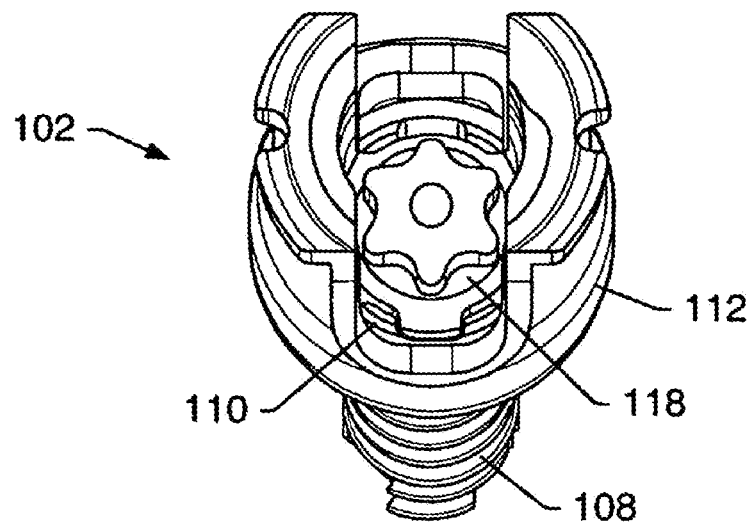

FIG. 9A depicts bone fastener 108 before insertion of the bone fastener into ring 110 positioned in collar 112. Splines 128 may be aligned with grooves 134 to allow passage of head 118 through ring 110 and into collar 112. FIG. 9B depicts bone fastener 108, ring 110, and collar 112 after the bone fastener has been rotated and head 118 has been coupled to seats in the ring to form bone fastener assembly 102. Inserting bone fastener 108 through opening 144 in collar 112 (depicted in FIG. 9A) may allow use of bone fasteners that have shanks and/or heads with larger diameters than can pass through slot 150. Bone fasteners with large diameter shanks may form a bone fastener assembly (threaded or otherwise) that securely fastens to vertebral bone during use.

A bone fastener may be rotatably positioned in a collar such that the bone fastener is able to move radially and/or rotationally relative to the collar (or the collar relative to the bone fastener) within a defined range of motion. The range of motion may be provided within a plane, such as by a hinged connection, or within a three-dimensional region, such as by a ball and socket connection. Motion of the bone fastener relative to the collar (or the collar relative to the bone fastener) may be referred to as "angulation" and/or "poly-axial movement".

Figure 10:
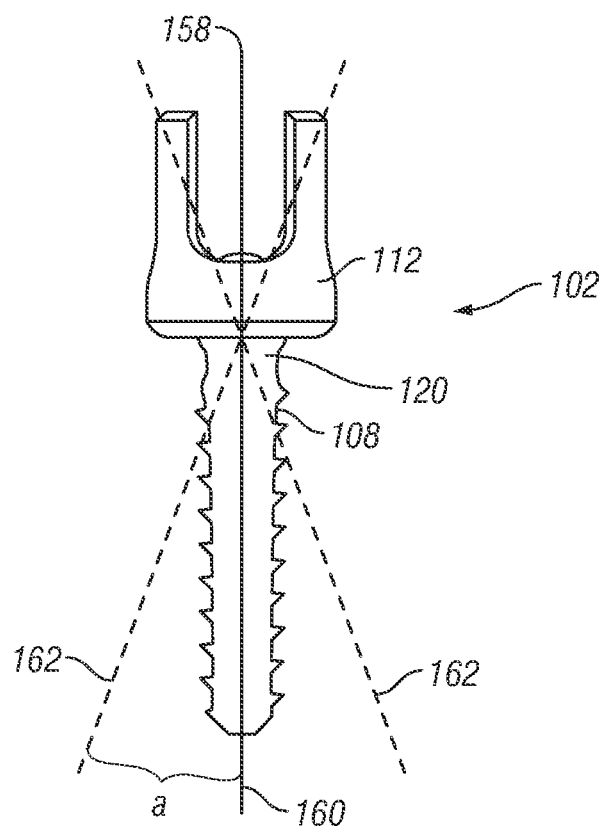
FIG. 10 depicts a front view of an embodiment of a bone fastener assembly with a collar that allows for angulation of a bone fastener relative to the collar in a conical range of motion that is symmetrical relative to an axis that passes through a central axis of the collar and a central axis of a bone fastener.

FIG. 10 depicts a front view of an embodiment of bone fastener assembly 102 with collar 112 that allows for angulation of bone fastener 108 relative to collar 112 in a conical range of motion. FIG. 10 depicts an example in which central axis 158 of collar 112 is aligned with central axis 160 of bone fastener 108. Bone fastener 108 may be angulated in a symmetrical conical range of motion characterized by angle $\alpha$ at about the aligned axes. Bone fastener 108 may be constrained from motion outside of limit axis 162 by contact between neck 120 of bone fastener 108 and collar 112. Alignment of axis 160 of bone fastener 108 with central axis 158 of collar 112 may be considered a neutral position relative to the range of motion. The alignment is a neutral position because bone fastener 108 may be angulated an equal amount in any direction from central axis 158. When a driver is inserted into bone fastener 108, axis 160 of bone fastener 108 may be substantially aligned with axis 158 of collar 112 to facilitate insertion of the bone fastener into a vertebral body.

In certain embodiments, a range of motion of a collar may be skewed from a full conical range of motion relative to aligned central axes of the collar and a bone fastener coupled to the collar. In some embodiments, a distal end of a collar may be shaped to skew, or bias, the range of motion from the range of motion depicted in FIG. 10. Additionally, body 140 of biased collar 112 may be shaped to restrict relative movement of bone fastener 108 (and/or the collar) to a skewed conical range of motion defined by limit axes 162. Other biased collars may be designed to selectively restrict poly-axial movement of collars and/or bone fasteners. In some embodiments, a biased collar may be attached to a detachable sleeve such that a surgeon performing a minimally invasive procedure may selectively align the portion of the collar with the greater range of motion as needed. When a biased collar of a bone fastener assembly is coupled to a detachable sleeve and a drive mechanism is coupled to a bone fastener of the bone fastener assembly, central axis 158 of collar 112 may align with central axis 160 of bone fastener 108 to facilitate insertion of the bone fastener into bone. In some embodiments, the bias of the collar may be so large that a flexible drive member is needed to drive the bone fastener into bone.

In some embodiments, one or more biased collars may be used in a spinal stabilization system. The spinal stabilization systems may be single-level systems or multi-level systems. Biased collars may be used to accommodate the increasing angle of the pedicle corridor for each lumbar vertebra. The angle may increase by about 5 degrees for each successive lumbar vertebra. Angulation of either or both collars of the bone fastener assemblies may allow fine adjustment of engagement angles of the bone fasteners. In addition, collar angulation may allow adjustment in the orientation of bone fasteners in a sagittal plane (i.e., to conform to lordosis of a spine) while still allowing the collars to be easily coupled with elongated member 104 (shown in FIG. 13). Elongated member 104 can be rigid, flexible, or a combination of both.

Figure 11:
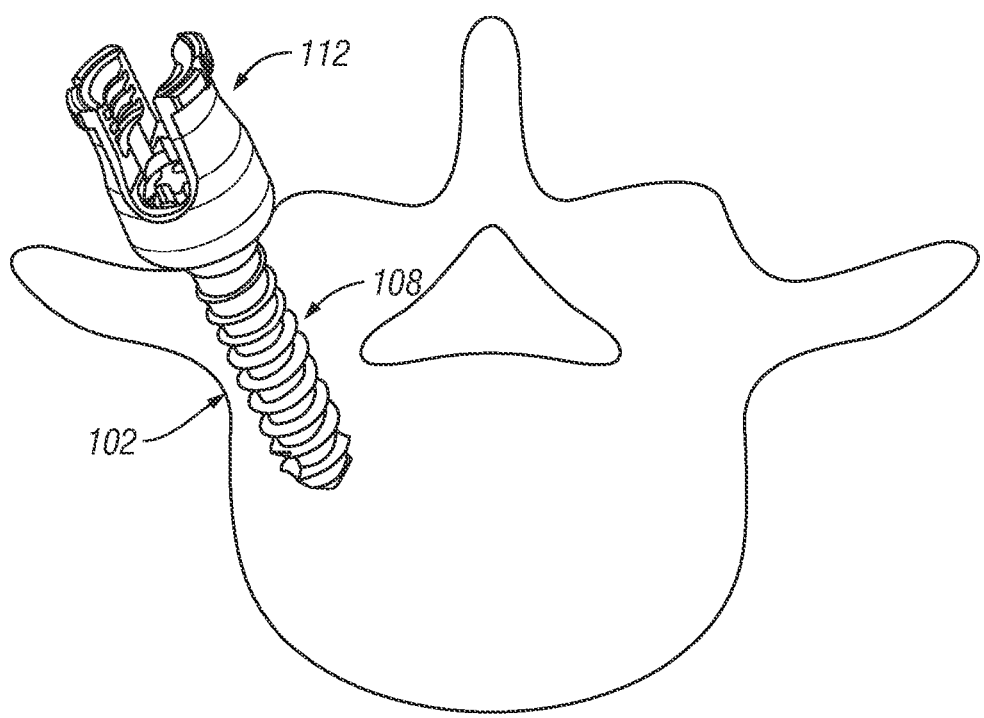
FIG. 11 depicts a simplified representation of an embodiment of a bone fastener assembly positioned in a vertebra.
Figure 12:
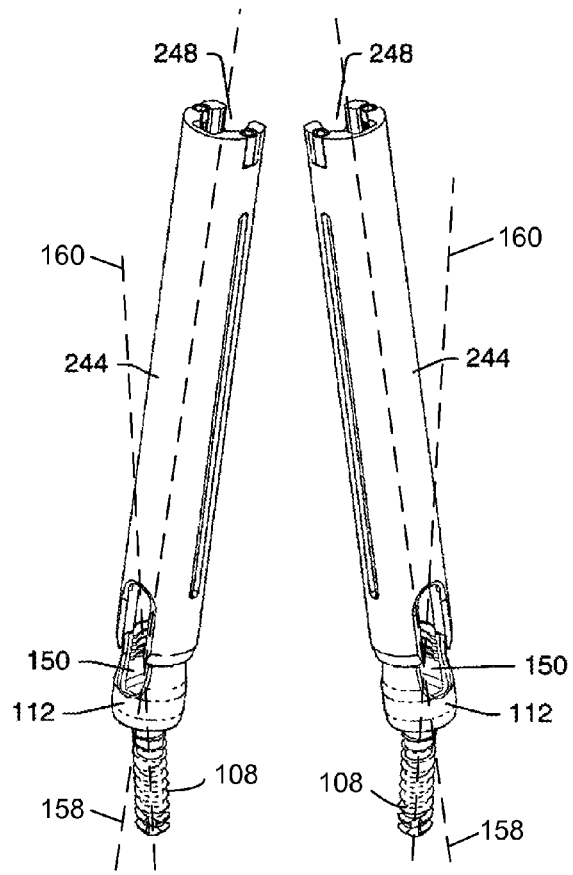
FIG. 12 depicts a perspective view of an embodiment of sleeves coupled to embodiments of bone fastener assemblies.
Figure 13:
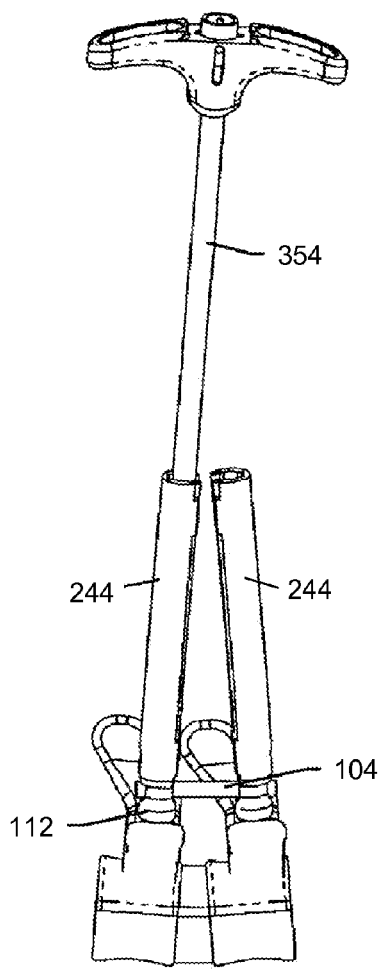
FIG. 13 depicts a perspective view of a tool coupled to an embodiment of a bone fastener assembly positioned in a vertebra.

FIG. 11 depicts a simplified representation of an embodiment of a bone fastener assembly positioned in a vertebra prior to coupling with an extender sleeve (shown in FIG. 12) and an elongated member (shown in FIG. 13). Elongated member 104 may be disposed in slots 150 of collars 112 and secured by closure members (not shown). More specifically, in a minimally invasive procedure, a closure member may be advanced through an extender sleeve into an opening in a collar to engage a portion of elongated member 104. In some embodiments, the engaged closure member may inhibit movement of elongated member 104 relative to collar 112. In some embodiments, a closure member may be cannulated or have a solid central core. A closure member with a solid central core may allow more contact area between the closure member and a driver used to couple the closure member to the collar. A closure member with a solid central core may provide a more secure connection to an elongated member than a cannulated closure member by providing contact against the elongated member at a central portion of the closure member as well as near an edge of the closure member. In some embodiments, a bottom surface of a closure member may include structure and/or texturing that promotes contact between the closure member and an elongated member. A portion of the structure and/or texturing may enter and/or deform an elongated member when the closure member is coupled to the elongated member. Having a portion of the closure member enter and/or deform the elongated member may couple the elongated member to the closure member and a bone fastener assembly so that movement of the elongated member relative to the bone fastener assembly is inhibited. Readers are directed to the above-referenced U.S. Pat. No. 7,250,052, for additional teachings on closure members.

In an embodiment, a bone fastener assembly and a closure member may be coupled with a running fit. A running fit (i.e., a fit in which parts are free to rotate) may result in predictable loading characteristics of a coupling of a bone fastener assembly and a closure member. Predictable loading characteristics may facilitate use of a closure member with a break-off portion designed to shear off at a predetermined torque. A running fit may also facilitate removal and replacement of closure members. In some embodiments, a closure member may include an interference fit (e.g., crest-to-root radial interference).

A detachable extender sleeve may be used in a minimally invasive procedure as a guide to install bone fasteners of a bone fastener assembly in vertebral bone. A detachable sleeve may be coupled to a collar of a bone fastener assembly. A distal end of a detachable sleeve may be tapered or angled to reduce bulk at a surgical site. Instruments may be inserted into the detachable sleeve to manipulate the bone fastener assembly. Movement of the detachable sleeve may alter an orientation of a collar relative to a bone fastener of the bone fastener assembly. In some embodiments, a detachable sleeve may be used as a retractor during a spinal stabilization procedure.

A detachable sleeve for a single-level vertebral stabilization system may include one or more channels in a wall of the detachable sleeve to allow access to an adjacent vertebra. For some single-level vertebral stabilization procedures, only single-channel detachable sleeves (i.e., detachable sleeves with a single channel in a wall of the detachable sleeve) may be used. For other single-level vertebral stabilization procedures, one or more multi-channel detachable sleeves (i.e., detachable sleeves with two or more channels in a wall of the detachable sleeve) may be used. Channels may provide flexibility to or enhance flexibility of a multi-channel detachable sleeve. In some embodiments, a proximal portion of a multi-channel detachable sleeve may have a solid circumference. A region of solid circumference in a multi-channel detachable sleeve may enhance stability of the multi-channel detachable sleeve. In some embodiments, a multi-channel detachable sleeve may be longer than a single-channel detachable sleeve.

Instruments may access a bone fastener assembly through a passage in a detachable sleeve. In some embodiments, a channel in a wall of a detachable sleeve may extend a full length of the detachable sleeve. In some embodiments, especially in embodiments of multi-channel detachable sleeves, a channel in a wall of a detachable sleeve may extend only a portion of the length of the detachable sleeve. In some embodiments, a channel in a wall of a detachable sleeve may extend 25%, 50%, 75%, 80%, 90%, 95% or more of the length of the detachable sleeve. A channel may extend to a distal end of a detachable sleeve such that an elongated member inserted in the channel may pass from the detachable sleeve into a slot of a collar of a bone fastener assembly coupled to the detachable sleeve. Readers are directed to the above-referenced U.S. Pat. No. 7,250,052, for additional teachings on detachable sleeves.

FIG. 12 depicts a perspective view of an embodiment of sleeves 244 coupled to embodiments of collars 112 of bone fastener assemblies. Sleeves 244 may include channels 248 extending from a distal end of sleeve 244 through a portion of sleeve 244. Channels 248 may allow instruments to be positioned and used to form a plane through soft tissue to one or more adjacent vertebrae. A distal end of sleeve 244 may include a flange that mates with a complementary flange on a collar of a bone fastener assembly. A distal end of sleeve 244 may be tapered to reduce bulk (e.g., reduce spin diameter) at a surgical site.

A detachable sleeve (or simply sleeve) may be coupled to a collar of a bone fastener assembly in various ways. When a sleeve is coupled to a collar, rotation and translation of the sleeve relative to the collar may be inhibited. A coupling system used to couple a sleeve to a collar should be simple, inexpensive to implement, and should not significantly weaken the mechanical strength of the collar and/or the sleeve. Examples of suitable coupling systems may include, but are not limited to, flanges, threaded connections, interlocking connections (e.g., ratcheting connection systems), and/or interference fits. Readers are directed to the above-referenced U.S. Pat. No. 7,250,052, for additional teachings on coupling the sleeves with the collars.

Through sleeve 244, a surgeon may position and use appropriate instruments to manipulate a bone fastener assembly that is coupled to a distal end of sleeve 244. An example of such an instrument is depicted in FIG. 13. FIG. 13 depicts a perspective view of driver 354 coupled, through an embodiment of sleeve 244, to an embodiment of a bone fastener assembly positioned in a vertebra. Driver 354 may be coupled to a closure member described above. With driver 354 positioned in sleeve 244, the driver may be rotated to advance the closure member, which is coupled to the driver, in collar 112 and secure elongated member 104 to the collar. When the closure member is snug and elongated member 104 is secured, driver 354 may be disengaged from the closure member and removed from sleeve 244. In an embodiment, driver 354 may be used to shear off the tool portion of the secured closure member. In some embodiments, the coupling portion of the driver may capture the sheared tool portion of the closure member. In certain embodiments, driver 354 may include a mechanism to dislodge a closure member and/or a tool portion of a closure member from the distal end of the driver.

As FIG. 13 illustrates, elongated member 104 connects a pair of bone fastener assemblies anchored in adjacent vertebrae. During surgery, a surgeon may need to correct the alignment and/or positions of the vertebrae prior to securing the elongated member to the bone fastener assemblies. For example, a vertebra may need to be turned to a desirable alignment and/or moved closer or further away from an adjacent vertebra. For applying angular correction to a vertebral body, a fixed angle bone screw, an example of which is shown in FIG. 6, is desired. A fixed angle bone screw may have the strength to withstand the corrective forces and allow the surgeon to manipulate a vertebra accordingly. However, the head portion and the shank portion of a fixed angle bone screw are fixed. When rotated, the bone screw threads in the shank can cause the bone screw to displace in the sagittal plane in or out of a pedicle. Also, the opening in the head portion of the bone screw must be perfectly aligned with an elongated member, such as a rod, is placed, which can also affect the depth of the shank in the pedicle.

Referring to FIG. 12, collars 112 can rotate poly-axially about the head of bone fasteners 108. Thus, through small incisions, a surgeon can manipulate sleeves 244 coupled to collars 112 to align slots 150 for receiving elongated member 104 without affecting the depths of the shanks of bone fasteners 108. As described above with reference to FIG. 10, angulation or poly-axial movement of bone fastener 108 relative to collar 112 is restricted to a range of motion. Alignment of axis 160 of bone fastener 108 with central axis 158 of collar 112 may be considered a neutral position relative to the range of motion. When a driver is inserted into bone fastener 108, axis 160 of bone fastener 108 may be substantially aligned with axis 158 of collar 112 to facilitate insertion of the bone fastener into a vertebral body. However, this neutral position is not locked and a surgeon cannot apply corrective forces to a vertebral body via a poly-axial bone fastener assembly.

Embodiments of a coaxially lockable poly-axial bone fastener assembly will now be described in detail with reference to FIGS. 14-24. A coaxially lockable poly-axial bone fastener assembly disclosed herein can be used in pedicle screw surgery and can be sized, placed, and locked in an identical manner to a poly-axial bone fastener. A coaxially lockable poly-axial bone fastener assembly disclosed herein has a collar, a bone fastener, and a coaxial locking mechanism. The collar of a coaxially lockable poly-axial bone fastener assembly is free to rotate about the axis of the bone fastener, so rotation of the collar during manipulation or while placing an elongated member into an opening of the collar does not affect the depth of the bone fastener in a pedicle. The coaxial locking mechanism can prevent multi-axial motion of the bone fastener inside the collar, so the collar can only spin about a central axis, making it mono-axial. Combining the functions and advantages of a poly-axial bone fastener assembly and a fixed angle bone screw, a coaxially lockable poly-axial bone fastener assembly disclosed herein can allow angular correction forces to be applied to a pedicle using instrumentation in a similar manner to a fixed angle screw and allow orientation of the collar for receiving an elongated member without affecting the depth of the shank of a bone fastener in the pedicle in a similar manner to a poly-axial bone fastener.

FIG. 14 depicts a perspective view of an embodiment of a bone fastener assembly and an embodiment of a coaxial locking mechanism. In some embodiments, components of coaxially lockable poly-axial bone fastener assembly 402 may include collar 412 and bone fastener 408. Collar 412 may include arms 442 defining opening 444 and slot 450. Opening 444 may be structured and sized to receive a closure member and slot 450 may be structured and sized to receive an elongated member as described above with reference to collar 112. Collar 412 may have additional features similar to those described above with reference to collar 112. For example, arms 442 of collar 412 may include ridges or flanges 454 and notches 456 for coupling to a detachable extender sleeve.

In some embodiments, components of coaxially lockable poly-axial bone fastener assembly 402 further comprise a coaxial locking mechanism. In the example of FIGS. 14 and 15, the coaxial locking mechanism is realized via a pinned c-clip that can be inserted into a corresponding cavity inside collar 412. More specifically, cavity 462 of collar 412 is particularly structured and dimensioned to accept c-clip 410 with a snug fit. Pine 460 is then inserted through holes 464 and 430 to pin c-clip 420 in place.

Bone fastener 408 may couple bone fastener assembly 402 to a vertebra. Bone fastener 408 may include shank 416, head 418, and neck 420. Shank 416 may include threading 422. In some embodiments, threading 422 may include self-tapping start 424. Self-tapping start 424 may facilitate insertion of bone fastener 408 into a pedicle. Head 418 of bone fastener 408 may include tool portion 426 for engaging bone fastener 408 with a surgical instrument. In some embodiments, a portion of neck 420 may be structured and sized to accommodate c-clip 410. In some embodiments, c-clip 410 is structured and sized to fit inside cavity 462. In some embodiments, c-clip 410 has a curved surface that, when inserted into cavity 462, matches a curved surface of collar 412. In some embodiments, bone fastener assembly 402 may permit poly-axial movements without c-clip 410 and may permit only mono-axial movements with c-clip 410 inserted into cavity 462.

FIG. 15 depicts a cross-sectional view of an embodiment of poly-axial bone fastener assembly 402 assembled with c-clip 410, which coaxially locks collar 412 and bone fastener 408. In the example shown in FIG. 15, bone fastener 408 may have passage 414 running through the full length of the bone fastener along axis 468. A guide wire may be placed through passage 414 so that bone fastener 408 may be inserted into a vertebra. Since collar 412 and bone fastener 408 are coaxially locked, if bone fastener 408 as inserted requires an angular orientation correction and/or if it is desired to move the vertebra, a surgeon may insert a driver into tool portion 426 of bone fastener 408 and apply corrective forces to bone fastener assembly 402 as a whole. The coaxiality of collar 412 and bone fastener 408 allows collar 412 to freely rotate about axis 468. A surgeon may therefore turn collar 412 to receive an elongated member into opening 450 without affecting shank 416 positioned in the vertebra.

Figure 16A:
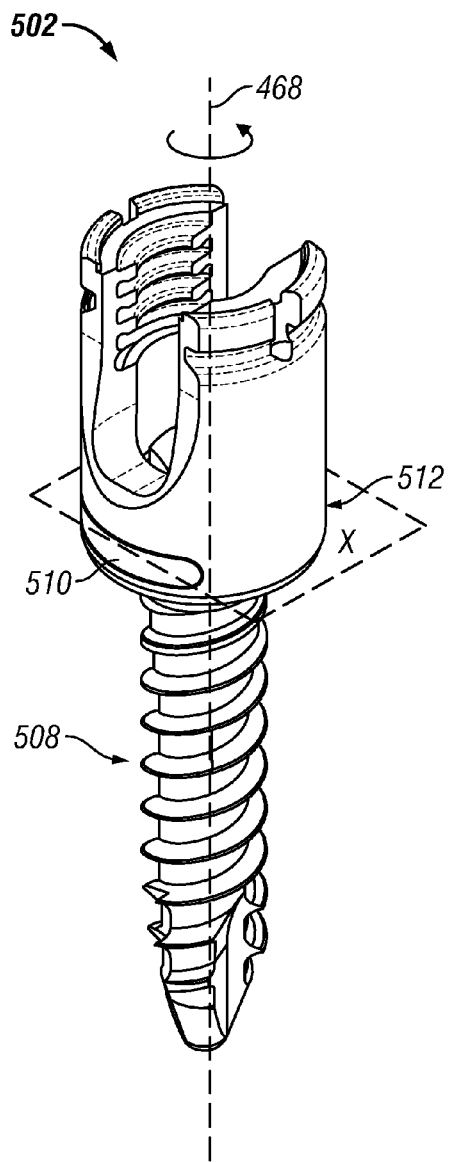
FIGS. 16A-16C depict views of an embodiment of a bone fastener assembly with a C-clip coaxial locking mechanism.
Figure 16B:
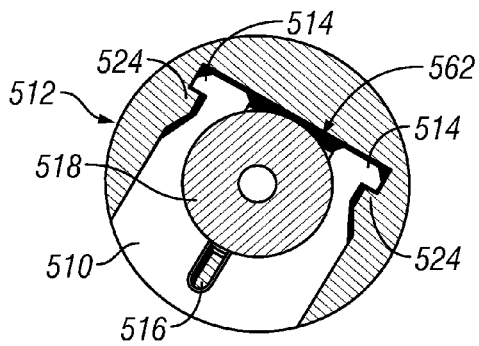
Figure 16C:
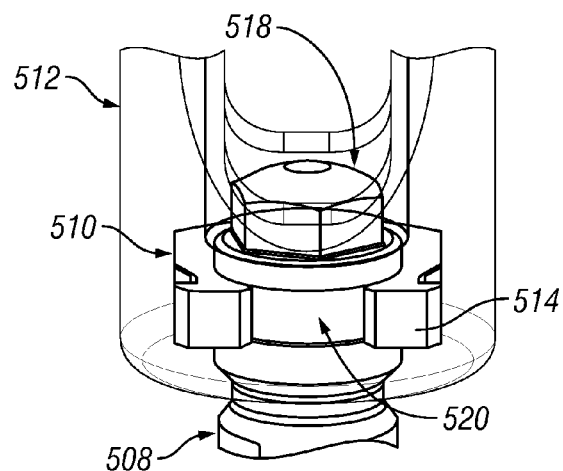
Figure 17A:
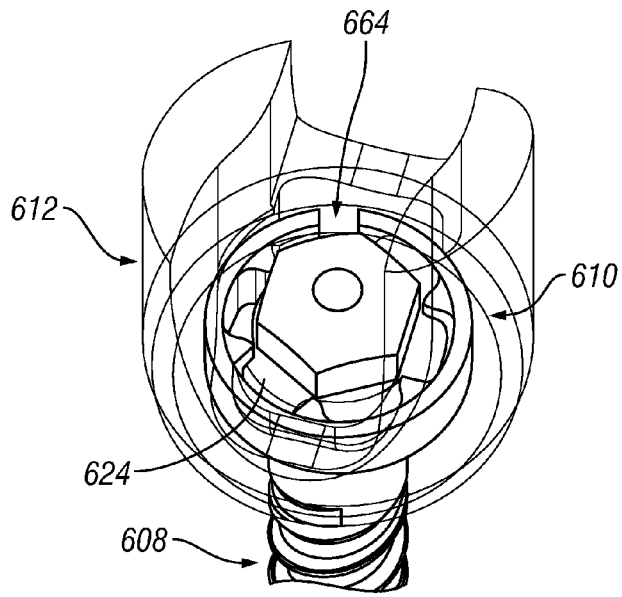
FIGS. 17A-17B depict views of an embodiment of a bone fastener assembly with a split-ring coaxial locking mechanism.
Figure 17B:
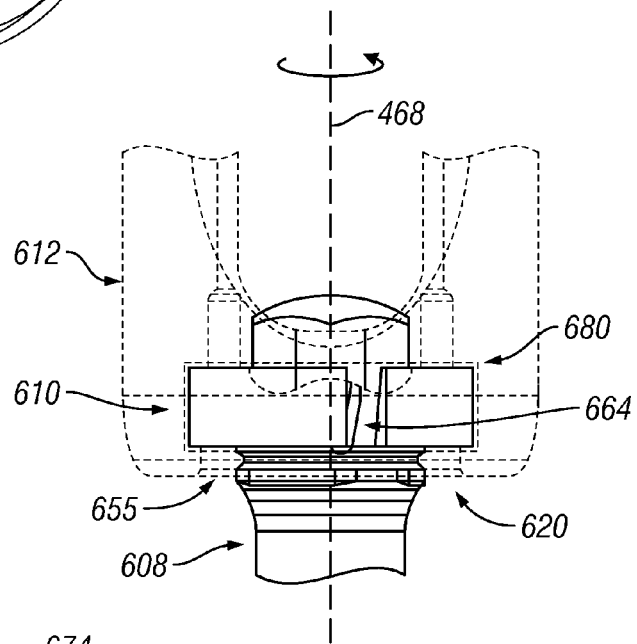
Figure 18:
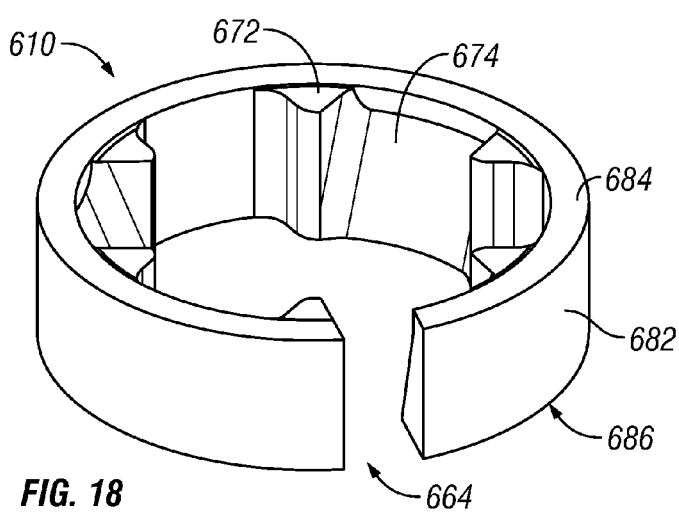
FIG. 18 depicts a perspective view of an embodiment of a coaxial locking ring.
Figure 19A:
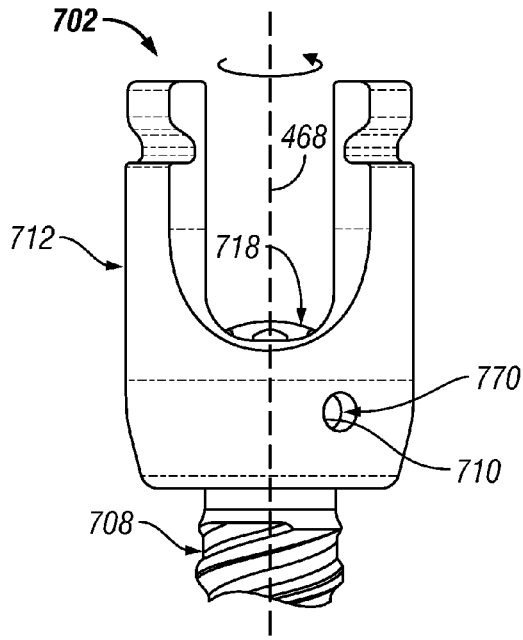
FIGS. 19A-19C depict views of an embodiment of a bone fastener assembly with a single pin coaxial locking mechanism.
Figure 19B:
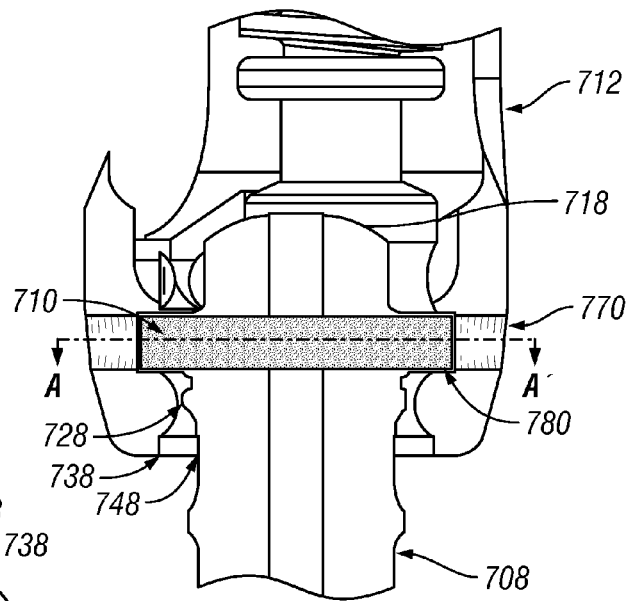
Figure 19C:
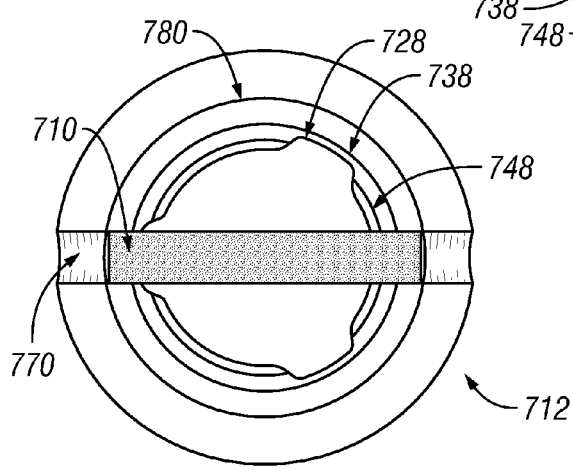
Figure 20A:
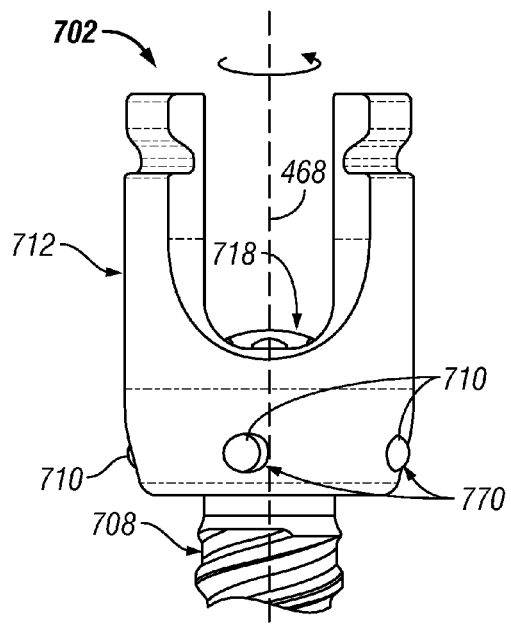
FIGS. 20A-20C depict views of an embodiment of a bone fastener assembly with a dual pin coaxial locking mechanism.
Figure 20B:
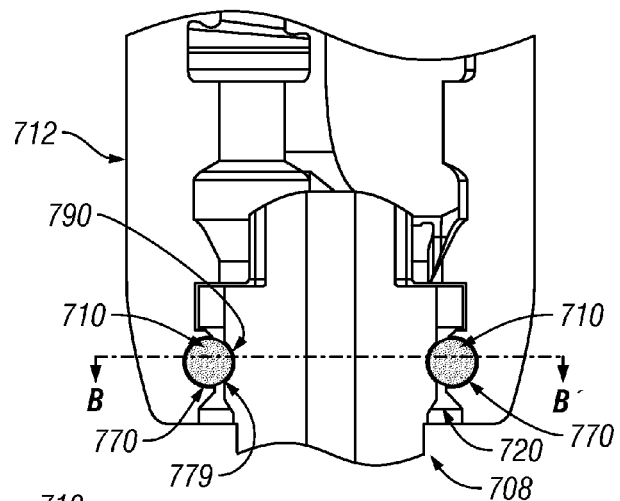
Figure 20C:
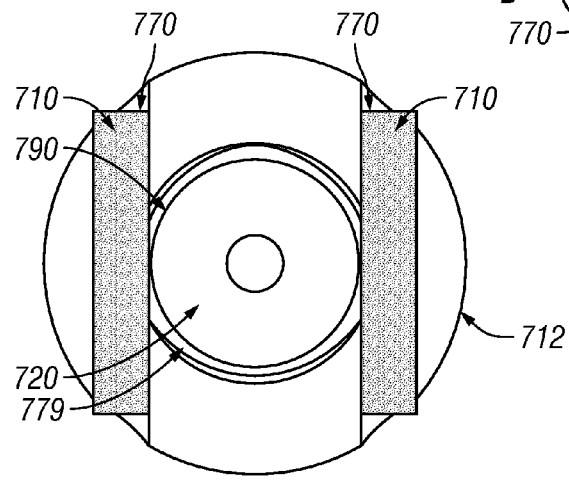
Figure 21:
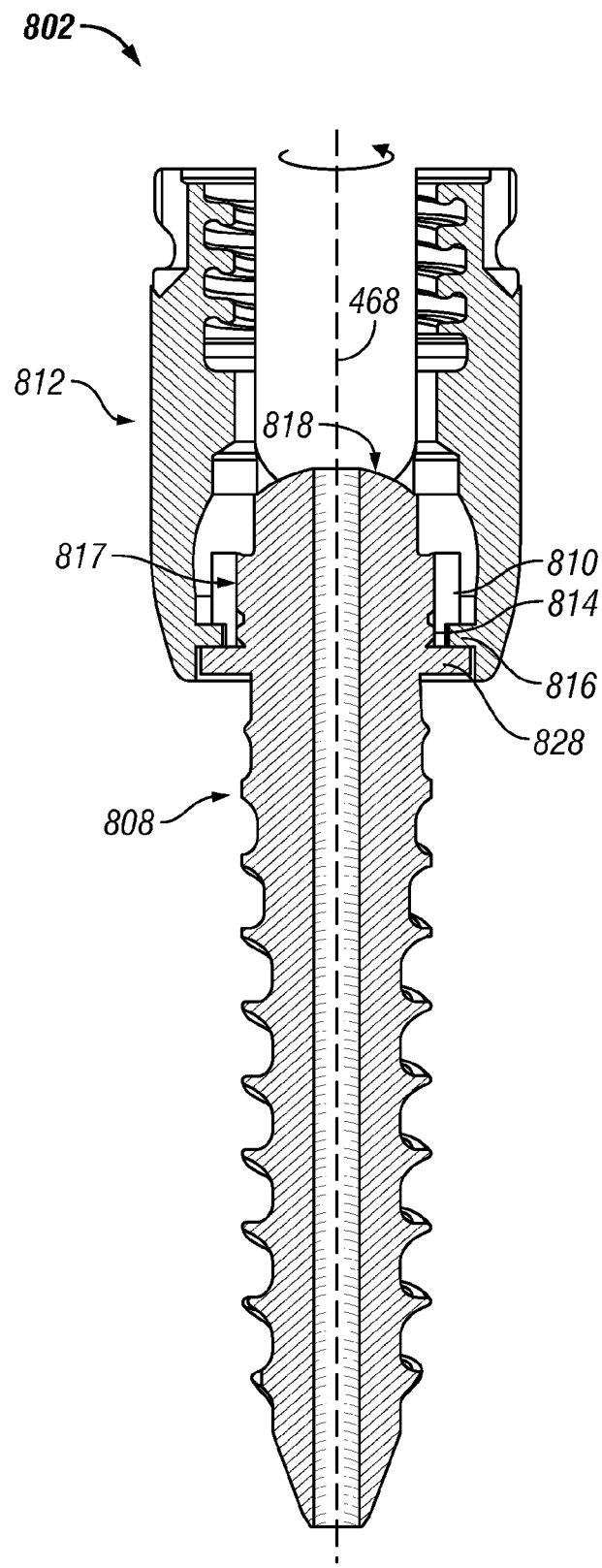
FIG. 21 depicts a cross-sectional view of an embodiment of a bone fastener assembly with a coaxial locking mechanism.
Figure 22:
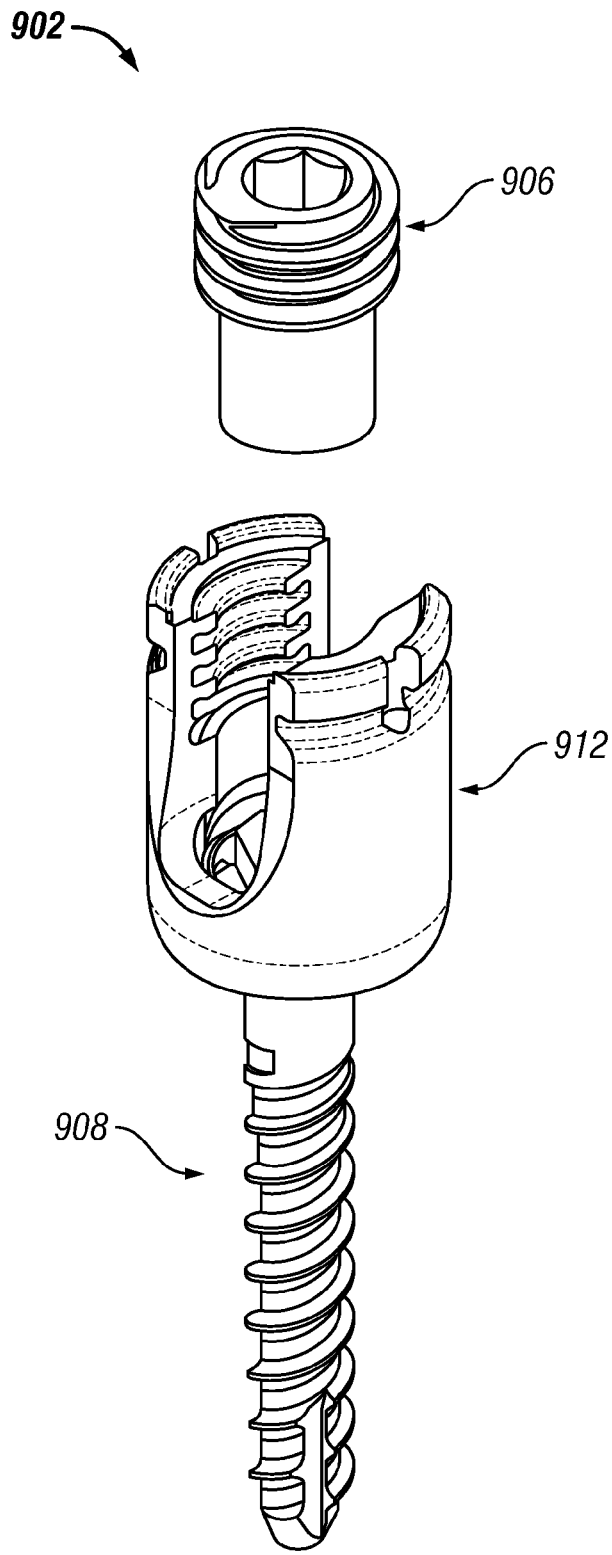
FIG. 22 depicts a perspective view of an embodiment of a bone fastener assembly and an embodiment of a poly-axial reversible coaxial locking mechanism.

The above-described coaxial locking mechanism coaxially locks a collar and a bone fastener of a poly-axial bone fastener assembly. More specifically, the coaxial locking mechanism coaxially locks a collar and a head portion of a bone fastener which is inside and coupled to the collar. Coaxially locking the collar and the bone fastener of a poly-axial bone fastener assembly can prevent poly-axial movements of the collar relative to the bone fastener while permitting coaxial rotation of the collar relative to the bone fastener. The above-described coaxial locking mechanism can be implemented in various ways. Another example of a coaxial locking mechanism with a c-clip design is shown in FIGS. 16A-16C. An example of a coaxial locking mechanism with a coaxial locking ring design is shown in FIGS. 17A-17C. An example of a coaxial locking ring is shown in FIG. 18. An example of a coaxial locking mechanism with a single pin design is shown in FIGS. 19A-19C. An example of a coaxial locking mechanism with a dual pin design is shown in FIGS. 20A-20C. An example of a coaxial locking mechanism with a threaded shank, an internal flange, and a top nut is shown in FIG. 21. An example of a top loading coaxial locking mechanism is shown in FIG. 22. Other ways to coaxially lock a collar and a bone fastener are also possible.

In the example shown in FIG. 15, the coaxial locking mechanism for a poly-axial bone fastener assembly comprises a c-clip and a cavity inside a collar of the bone fastener assembly for receiving the c-clip. The c-clip engages a portion of a neck of a bone fastener inside the cavity of the collar, preventing poly-axially movements of the collar relative to the bone fastener while permitting coaxial rotation of the collar with respect to a central axis of the bone fastener. A pin is then inserted into an opening in the collar to lock the c-clip to the collar and thus coaxially locking the collar and the bone fastener.

In the example shown in FIGS. 16A-16C, the coaxial locking mechanism for poly-axial bone fastener assembly 502 comprises c-clip 510 and cavity 562 inside collar 512 of bone fastener assembly 502 for receiving c-clip 510. A cross-sectional view along plane x is depicted in FIG. 16B. C-clip 510 engages a portion of neck 520 of bone fastener 508 inside cavity 562 of collar 512, preventing poly-axially movements of the collar relative to the bone fastener while permitting coaxial rotation of the collar with respect to central axis 468 of bone fastener assembly 502. C-clip 510 comprises narrow opening or slit 516 and hooks 514 structured to snap locks into place inside collar 512. Cavity 562 of collar 512 may be structured, dimensioned, and sized accordingly. For example, cavity 562 may comprise shoulders 524 that are sloped to narrow a width of cavity 562 towards the back of cavity 562 and that are angled to form pockets behind the narrowed passage to catch hooks 514 and lock c-clip 510 in place inside cavity 562, as shown in the perspective view of FIG. 16C. Slit 516 allows a width of c-clip 510 to be sufficiently reduced to pass a narrow passage inside cavity 562 and sharply sprang back into the pockets behind shoulders 524 after passing the narrow passage.

In some embodiments, a coaxial locking ring may be utilized in a coaxial locking mechanism for a poly-axial bone fastener assembly. FIGS. 17A-17B show a portion of one embodiment of poly-axial bone fastener assembly 602 with coaxial locking ring 610. In the example of FIGS. 17A-17B, collar 612 and bone fastener 608 of poly-axial bone fastener assembly 602 are coaxially locked via coaxial locking ring 610. In some embodiments, coaxial locking ring 610 may have narrow opening or slit 664. Slit 664 may allow coaxial locking ring 610 to be slightly collapsed for loading into collar 612 to a snug fit. Coaxial locking ring 610 may be loaded into collar 612 from the top of collar 612 or from bottom opening 655.

FIG. 18 depicts a perspective view of an embodiment of coaxial locking ring 610 with square corners. In some embodiments, coaxial locking ring 610 may comprise outer surface 682. In some embodiments, outer surface 682 of coaxial locking ring 610 is straight in a direction parallel to axis 468. In some embodiments, top surface 684 joins outer surface 682 at a 90-degree angle and bottom surface 686 also joins outer surface 682 at a 90-degree angle. As FIG. 17B illustrates, from a side view, it appears that coaxial locking ring 610 has square corners and fits snuggly inside groove 680 that is dimensioned with an appropriate height and 90-degree angle corners to fit coaxial locking ring 610. Groove 680 inside collar 612 has a diameter slightly larger than bottom opening 655. In some embodiments, the diameter of groove 680 inside collar 612 is slightly smaller than coaxial locking ring 610 in its neutral position such that, in addition to the depth of groove 680 inside collar 612, coaxial locking ring 610 is held in position inside groove 680 by tension.

In some embodiments, outer surface 682 of coaxial locking ring 610 may have a smooth finish. In some embodiments, outer surface 682 may be surface treated or include coatings and/or coverings. Surface treatments, coatings, and/or coverings may be used to adjust frictional and/or wear properties of the outer surface of the ring.

In some embodiments, coaxial locking ring 610 may comprise internal projections 672 and sloped recesses 674 arranged in an alternating pattern. In some embodiments, the head portion of bone fastener 608 may comprise sloped projections 624 and corresponding recessed areas arranged to accommodate sloped recesses 674 and projections 672 inside coaxial locking ring 610. Once loaded, the square corners on the coaxial locking ring and the groove of the collar only allow the collar to rotate about axis 468.

FIGS. 19A-19C depict representative views of an embodiment of a bone fastener assembly with a single pin coaxial locking mechanism. FIG. 19A depicts a side view of a portion of poly-axial bone fastener assembly 702. Poly-axial bone fastener assembly 702 may have collar 712 and bone fastener 708. Collar 712 may have pin hole 770. Head 718 of bone fastener 708 may have a pin hole (not shown in FIG. 19A) corresponding to pin hole 770 of collar 712. FIG. 19B depicts a cross-sectional view of a portion of poly-axial bone fastener assembly 702. As it can be seen in FIG. 19B, pin 710 has a side profile with square corners. Pin 710 may be press fit into head 718 of bone fastener 708 through pin hole 770 of collar 712. Collar 712 may comprise track or groove 780 having a side profile complementary to that of pin hole 770, as shown in FIG. 19B. Groove 780 may be structured to accommodate pin 710 and permit pin 710 to rotate about axis 468 inside groove 780 of collar 712. As it can be seen from FIG. 19B, groove 780 also have square corners. These square corners help to ensure that pin 710 and hence bone fastener 708 can only spin about axis 468, coaxially locking bone fastener 708 and collar 712. In some embodiments, bone fastener 708 may be loaded into collar 712 from bottom opening 748. Protruding features 728 of bone fastener 708 and shoulders 738 of collar 712 may be structured to prevent bone fastener 708 from backing out of collar 712 after loading. FIG. 19C depicts a simplified cross-sectional view of FIG. 19B along line A-A'. As it can be seen in FIG. 19C, groove 780 has an accommodating diameter that can allow pin 710 to spin freely inside groove 780 of collar 712. Groove 780 may be slightly larger than pin hole 770.

FIGS. 20A-20C depict representative views of an embodiment of a bone fastener assembly with a dual pin coaxial locking mechanism. FIG. 20A depicts a side view of a portion of poly-axial bone fastener assembly 702. Poly-axial bone fastener assembly 702 may have collar 712 and bone fastener 708. Collar 712 may have pin holes 770. Pins 710 may be press fit into pin holes 770 of collar 712. FIG. 20B depicts a cross-sectional view of a portion of poly-axial bone fastener assembly 702. As it can be seen in FIG. 20B, neck 720 of bone fastener 708 may have track or groove 790. Groove 790 of bone fastener 708 may have a contoured surface defined by edges 779. Groove 790 may accommodate portions of pins 710. Pins 710 may be rotated about axis 468 along groove 790 of neck 720 of bone fastener 708. FIG. 20C depicts a simplified cross-sectional view of FIG. 20B along line B-B'. Bone fastener 708 may be loaded into collar 712 from a bottom opening thereof. As it can be seen in FIG. 20C, once press fit into pin holes 770 of collar 712, portions of pins 710 can be in contact or in close contact with portions of groove 790 of neck 720 of bone fastener 708. As FIGS. 21B and 21C illustrate, pins 710 can coaxially lock bone fastener 708 and collar 712 in place while allowing collar 712 to rotate about axis 468.

FIG. 21 depicts a cross-sectional view of an embodiment of a bone fastener assembly with a coaxial locking mechanism. In this example, bone fastener assembly 802 comprises collar 812 and bone fastener 808. Collar 812 may have internal flange 816. Bone fastener 808 may comprise head 818 and shoulder 828. Top nut 810 may be female threaded and portion 817 of head 818 of bone fastener 808 may be male threaded. Top nut 810 may be loaded into collar 812 from the top or the bottom of collar 812. Bone fastener 808 may be coupled to collar 812 by screwing top nut 810 onto threaded portion 817 of bone fastener 808. Bottom 814 of top nut 810 has a smaller outer diameter. As it can be seen from FIG. 21, as top nut 810 is screwed onto head 818 of bone fastener 808, flange 816 of collar 812 may be trapped but not pinched between top nut 810 and shoulder 828 of bone fastener 808. This allows collar 812 to rotate about axis 468 while preventing poly-axial movements of collar 812 relative to bone fastener 808. In some embodiments, bone fastener 808 may be cannulated.

FIG. 22 depicts a perspective view of an embodiment of bone fastener assembly 902. Bone fastener assembly 902 may comprise collar 912 and bone fastener 908. Collar 912 and bone fastener 908 may be coaxially locked via poly-axial reversible coaxial locking top 906. An example of a poly-axial reversible coaxial locking top is depicted in FIGS. 23A-23B.

Figure 23A:
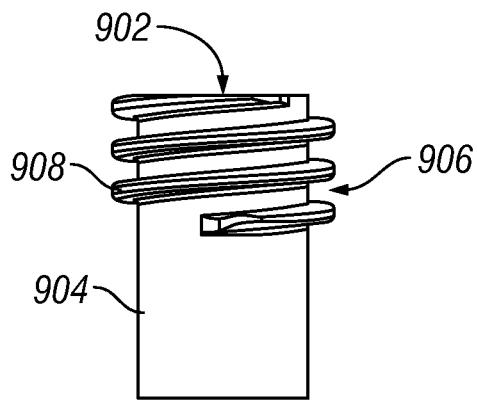
FIGS. 23A-23B depict views of an embodiment of a poly-axial reversible coaxial locking top.
Figure 23B:
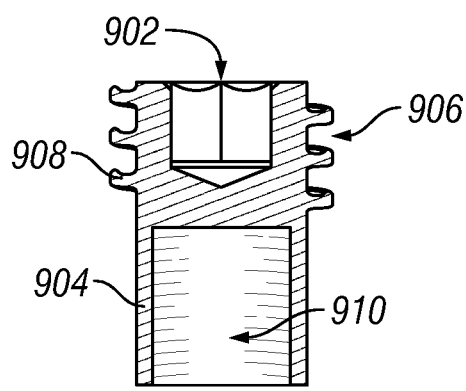

FIG. 23A is a side view of an embodiment of poly-axial reversible coaxial locking top 906 and FIG. 23B is a cross-sectional view of FIG. 23A. Coaxial locking top 906 may have body 904, threaded portion 908, and tool portion 902. Body 904 of coaxial locking top 906 may have hollow interior 910.

Figure 24:
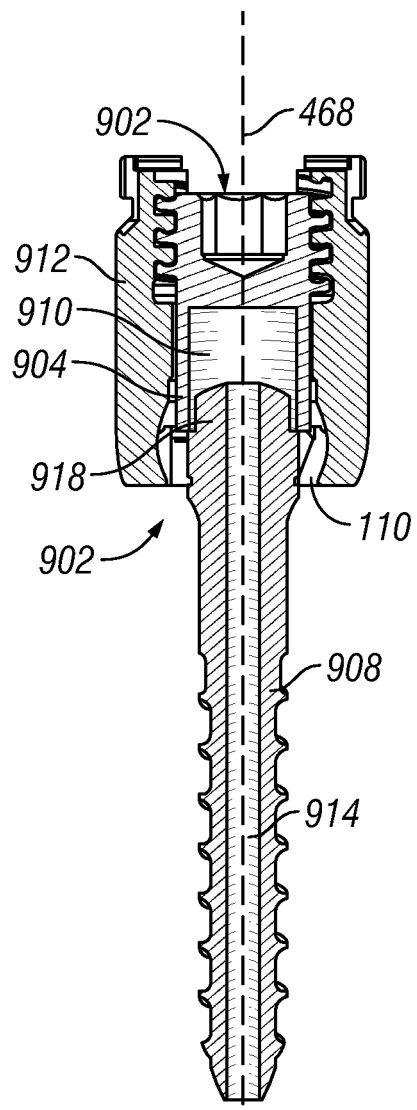
FIG. 24 depicts a cross-sectional view of an embodiment of a bone fastener assembly with a poly-axial reversible coaxial locking mechanism.

FIG. 24 depicts a cross-sectional view of an embodiment of bone fastener assembly 902 with an embodiment of poly-axial reversible coaxial locking top 906 threaded into collar 912 of bone fastener assembly 902. In some embodiments, bone fastener 908 may have passage 914. As it can be seen in FIG. 24, hollow interior 910 of coaxial locking top 906 may be dimensioned to fit over head 918 of bone fastener 908 and prevent collar 912 from pivoting relative to bone fastener 908. Thus, with coaxial locking top 906 screwed in place inside collar 912, collar 912 can rotate about axis 468 but cannot pivot relative to bone fastener 908. Coaxial locking top 906 can be unscrewed or otherwise removed from collar 912 to return bone fastener assembly 902 to poly-axial movements. This reversibility provides a surgeon with additional advantages.

More specifically, the surgeon can insert a poly-axial bone fastener assembly into a vertebra as described above and convert the poly-axial bone fastener assembly into a mono-axial bone screw when desired during surgery by simply screwing coaxial locking top 906 in place inside the collar. As an example, poly-axial bone fastener assembly 902 may be identical to poly-axial bone fastener assembly 102 having ring 110 as described above. Using the mono-axial bone screw thus converted from poly-axial bone fastener assembly 102, the surgeon can apply corrective forces to move the vertebra. If desired, the surgeon may rotate the collar coaxially relative to the bone fastener with coaxial locking top 906 in place inside the collar. The surgeon may remove coaxial locking top 906 from the collar to regain poly-axial movements of the collar relative to the bone fastener. An elongated member such as a rod can then be positioned in the collar of the poly-axial bone fastener assembly as described above.

Embodiments of a coaxially lockable poly-axial bone fastener assembly have now been described in detail. Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the disclosure.

It is to be understood that the forms of the disclosure shown and described herein are to be taken as examples of embodiments. Elements and materials may be substituted for or implemented from those illustrated and described herein, as would be apparent to one skilled in the art after having the benefit of the disclosure. Changes may be made in the elements or to the features described herein without departing from the spirit and scope of the disclosure as set forth in the following claims and their legal equivalents.

What is claimed is:

1. A coaxially lockable poly-axial bone fastener assembly, comprising:
a bone fastener having a head, a shank, and a neck between the head and the shank, wherein the neck has a smaller outer diameter than adjacent portions of the head and the shank;
a collar having an opening for receiving said bone fastener; and
a coaxial locking mechanism for locking said collar and said bone fastener, wherein said coaxial locking mechanism comprises a coaxial lock, wherein said collar further comprises a cavity structured to accommodate said coaxial lock, wherein a portion of said neck of said bone fastener is structured to mate with said coaxial lock, wherein said coaxial lock is positioned in said cavity of said collar and mates with said portion of said neck of said bone fastener, wherein said coaxial locking mechanism prevents poly-axial movements of said collar relative to said bone fastener while permitting coaxial rotation of said collar relative to said bone fastener, wherein prevention of said poly-axial movements allows angular correction forces to be applied to a pedicle to which said shank of said bone fastener is affixed, and wherein permission of said coaxial rotation allows orientation of said collar relative to said shank of said bone fastener for receiving an elongated member without affecting a depth of said shank of said bone fastener in said pedicle.

2. The coaxially lockable poly-axial bone fastener assembly of claim 1, wherein said coaxial lock comprises a c-clip.

3. The coaxially lockable poly-axial bone fastener assembly of claim 2, wherein said c-clip comprises at least one pin hole, wherein said coaxial locking mechanism further comprises at least one pin, wherein said collar further comprises at least one corresponding pin hole, and wherein said at least one pin of said coaxial locking mechanism couples said c-clip and said collar through said at least one corresponding pin hole of said collar, said cavity of said collar, and said at least one pin hole of said c-clip.

4. The coaxially lockable poly-axial bone fastener assembly of claim 2, wherein said c-clip comprises a slit and hooks, wherein said cavity of said collar comprises shoulders, a passage defined by said shoulders, and pockets formed behind said shoulders and structured to receive said hooks of said c-clip.

5. The coaxially lockable poly-axial bone fastener assembly of claim 4, wherein said c-clip comprises square corners.

6. The coaxially lockable poly-axial bone fastener assembly of claim 1, wherein said coaxial lock comprises a split ring with square corners.

7. The coaxially lockable poly-axial bone fastener assembly of claim 1, wherein said coaxial lock comprises a single pin, wherein said collar and said portion of said neck of said bone fastener further comprise corresponding pin holes dimensioned to accommodate said single pin, and wherein said single pin is press fit into said corresponding pin holes of said collar and said portion of said neck of said bone fastener.

8. The coaxially lockable poly-axial bone fastener assembly of claim 7, wherein said collar further comprises a track inside said collar, wherein said track is structured to accommodate said single pin, and wherein said coaxial rotation of said collar relative to said bone fastener further comprises rotation of said single pin along said track inside said collar.

9. The coaxially lockable poly-axial bone fastener assembly of claim 1, wherein said coaxial lock comprises side pins, wherein said collar and said portion of said neck of said bone fastener further comprise corresponding pin holes dimensioned to accommodate said side pins, and wherein said side pins are press fit into said corresponding pin holes of said collar and said portion of said neck of said bone fastener.

10. The coaxially lockable poly-axial bone fastener assembly of claim 9, wherein said portion of said neck of said bone fastener further comprises a track, wherein said track is structured to accommodate said side pins, and wherein said coaxial rotation of said collar relative to said bone fastener further comprises movement of said side pins along said track on said portion of said neck of said bone fastener.

11. A coaxially lockable poly-axial bone fastener assembly, comprising:
  a bone fastener having a head, a shank extending from the head along a longitudinal axis of the bone fastener, and a neck between the head and the shank, wherein the neck has a smaller outer diameter than adjacent portions of the head and the shank;
  a collar having an opening for receiving the bone fastener and a longitudinal axis; and
  a coaxial locking mechanism positionable between the head and the shank for selectively locking the collar and the bone fastener into a mono-axial configuration such that the longitudinal axis of the bone fastener is co-axial with the longitudinal axis of the collar;
  wherein in a poly-axial configuration the collar is permitted to pivot relative to the bone fastener such that the longitudinal axis of the collar may be positioned at one of a plurality of angular positions relative to the longitudinal axis of the bone fastener and the collar is permitted to rotate relative to the bone fastener about the longitudinal axis of the collar; and
  wherein in the mono-axial configuration the collar is prevented from pivoting relative to the bone fastener such that the longitudinal axis of the collar is fixed co-axially with the longitudinal axis of the bone fastener while permitting the collar to rotate relative to the bone fastener about the longitudinal axis of the collar.

12. The coaxially lockable poly-axial bone fastener of claim 11, wherein the coaxial locking mechanism comprises a coaxial lock and the collar comprises a cavity structured to accommodate the coaxial lock.

13. The coaxially lockable poly-axial bone fastener of claim 12, wherein the neck is structured to mate with the coaxial lock.

14. The coaxially lockable poly-axial bone fastener of claim 13, wherein in the mono-axial configuration the coaxial lock is positioned in the cavity of the collar and mates with the neck of the bone fastener to prevent pivoting of the collar relative to the bone fastener.

* * * * *

UNITED STATES PATENT AND TRADEMARK OFFICE
CERTIFICATE OF CORRECTION

| | | |
|---|---|---|
| PATENT NO. | : 8,603,145 B2 | Page 1 of 1 |
| APPLICATION NO. | : 12/336404 | |
| DATED | : December 10, 2013 | |
| INVENTOR(S) | : Charles R. Forton et al. | |

It is certified that error appears in the above-identified patent and that said Letters Patent is hereby corrected as shown below:

In the Specification

Column 1, Line 39: delete "(procsses)" and insert -- (processes) --.

Column 7, Line 3: delete "stabilizatoin" and insert -- stabilization --.

Signed and Sealed this
Fourth Day of March, 2014

Michelle K. Lee
*Deputy Director of the United States Patent and Trademark Office*